(12) United States Patent
Giordano et al.

(10) Patent No.: US 7,598,052 B2
(45) Date of Patent: Oct. 6, 2009

(54) EXPRESSION PROFILE OF THYROID CANCER

(75) Inventors: Thomas Giordano, Ann Arbor, MI (US); Ronald Koenig, Ann Arbor, MI (US); Rork Kuick, Dexter, MI (US); Samir Hanish, Seattle, WA (US); Yuri Nikiforov, Pittsburgh, PA (US); Dafydd G. Thomas, Fenton, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 120 days.

(21) Appl. No.: 11/545,586

(22) Filed: Oct. 10, 2006

(65) Prior Publication Data
US 2008/0044824 A1 Feb. 21, 2008

Related U.S. Application Data

(60) Provisional application No. 60/725,389, filed on Oct. 11, 2005.

(51) Int. Cl.
G01N 33/574 (2006.01)
G01N 33/53 (2006.01)
C12Q 1/68 (2006.01)
C12P 21/08 (2006.01)
C07K 16/00 (2006.01)

(52) U.S. Cl. .......................... 435/7.23; 435/6; 435/7.1; 530/387.7

(58) Field of Classification Search .................. None
See application file for complete search history.

(56) References Cited

U.S. PATENT DOCUMENTS

| | | | | |
|---|---|---|---|---|
| 7,319,011 B2* | 1/2008 | Riggins et al. | ............... | 435/7.1 |
| 2005/0074798 A1* | 4/2005 | Sukumar et al. | ............... | 435/6 |

OTHER PUBLICATIONS

Tzelepi, Tsamandas, Vlotinou, Vagianos, and Scopa. Tight junctions in thyroid carcinogenesis: diverse expression of claudin-1, claudin-4, claudin-7 and occludin in thyroid neoplasms. Modern Pathology, 2008. vol. 21, pp. 22-30.*
Lewin. Genes IV. 1990. Oxford University Press, p. 810.*
Tanaka, Umeki, Yamamoto, Sugiyama, Noguchi, and Ohtaki. Immunohistochemical loss of thyroid peroxidase in papillary thyroid carcinoma: strong suppression of peroxidase gene expression. Journal of Pathology, 1996. vol. 179, pp. 89- 94.*
Allander et al., "Gastrointestinal stromal tumors with KIT mutations exhibit a remarkably homogeneous gene expression profile" Cancer Res, 200161, 8624-8.
Baker, "The immune response to papillary thyroid cancer" J Clin Endocrinol Metab, 1995, 80, 3419-20.
Begum et al., "BRAF mutations in anaplastic thyroid carcinoma: implications for tumor origin, diagnosis and treatment" Mod Pathol, 2004, 17, 1359-63.

Bertucci et al., "Identification and validation of an ERBB2 gene expression signature in breast cancers" Oncogene, 2004, 23, 2564-75.
Bongarzone & Pieriotte, "The molecular basis of thyroid epithelial tumorigenesis" Tumori, 2003, 89, 514-6.
Bongarzone et al., "High frequency of activation of tyrosine kinase oncogenes in human papillary thyroid carcinoma" Oncogene, 1989, 4, 1457-62.
Bounacer et al., "High prevalence of activating ret proto-oncogene rearrangements, in thyroid tumors from patients who had received external radiation" Oncogene, 1997, 15, 1263-73.
Califano et al., "Analysis of Gene Expression Microarrays for Phenotype Classification" 2000 Proc. Int. Conf. Intell. Sys. Mol. Biol. 8 75-85.
Capella et al., "Ras oncogene mutations in thyroid tumors: polymerase chain reaction-restriction-fragment-length polymorphism analysis from paraffin-embedded tissues" Diagn Mol Pathol, 1996, 5, 45-52.
Cohen et al., "BRAF mutation in papillary thyroid carcinoma" J Natl Cancer Inst, 2003, 95, 625-7.
Demicco, Am J Clin Pathol, 2003120, 803, 2003.
Donghi et al., "Gene p53 mutations are restricted to poorly differentiated and undifferentiated carcinomas of the thyroid gland" J Clin Invest, 1993, 91, 1753-60.
Fagin, "Perspective: lessons learned from molecular genetic studies of thyroid cancer—insights into pathogenesis and tumor-specific therapeutic targets" Endocrinology, 2002, 143, 2025-8.
Giordano et al., "Distinct transcriptional profiles of adrenocortical tumors uncovered by DNA microarray analysis" Am J Pathol, 2003, 162, 521-31.
Hedenfalk et al., "Gene-expression profiles in hereditary breast cancer" N Engl J Med, 2001344, 539-48, 2001.
Ho et al., "Mutations of BRAF and KRAS precede the development of ovarian serous borderline tumors" Cancer Res 2004, 64, 6915-8.
Huang et al., "Gene expression in papillary thyroid carcinoma reveals highly consistent profiles" Proc Natl Acad Sci U S A, 2001, 98, 15044-9.
Jazaeri et al., "Gene expression profiles of BRCA1-linked, BRCA2-linked, and sporadic ovarian cancers" J Natl Cancer Inst, 2002, 94, 990-1000.
Juhasz & Farid, "Immune response to papillary thyroid carcinoma" J Clin Endocrinol Metab, 1996, 81, 4175-6.
Karga et al., "Ras oncogene mutations in benign and malignant thyroid neoplasms" J Clin Endocrinol Metab, 1991, 73, 832-6.
Kimura et al., "High prevalence of BRAF mutations in thyroid cancer: genetic evidence for constitutive activation of the RET/PTC-RAS-BRAF signaling pathway in papillary thyroid carcinoma" Cancer Res, 2003, 63, 1454-7.
Kishida et al., "Enhancement of the aquaporin adipose gene expression by a peroxisome proliferator-activated receptor gamma" J Biol Chem 2001;276:48572.

(Continued)

*Primary Examiner*—David J. Blanchard
*Assistant Examiner*—Anne M. Gussow
(74) *Attorney, Agent, or Firm*—Casimir Jones, S.C.

(57) ABSTRACT

The present invention relates to compositions and methods for cancer diagnostics, including but not limited to, cancer markers. In particular, the present invention provides gene expression profiles associated with thyroid cancers. Genes identified as cancer markers using the methods of the present invention find use in the diagnosis and characterization of thyroid cancer. In addition, the genes provide targets for cancer drug screens and therapeutic applications.

4 Claims, 9 Drawing Sheets

OTHER PUBLICATIONS

Kroll et al., "PAX8-PPARgamma1 fusion oncogene in human thyroid carcinoma" Science 2000;289:1357.

Lowinger et al., "Design and discovery of small molecules targeting raf-1 kinase" Curr Pharm Des, 2002, 8, 2269-78.

Lynch et al., N Engl J Med, 2004, 35, 2129-39.

Lyons et al., "Discovery of a novel Raf kinase inhibitor" Endocr Relat Cancer, 2001, 8, 219-25.

Moretti et al., "Molecular pathogenesis of thyroid nodules and cancer" Baillieres Best Pract Res Clin Endocrinol Metab, 2000, 14, 517-39.

Namba et al., "Point mutations of ras oncogenes are an early event in thyroid tumorigenesis" Mol Endocrinol,1990, 4, 1474-9.

Nardone et al., "c-Met expression in tall cell variant papillary carcinoma of the thyroid" Cancer, 2003, 98, 1386-93.

Nikiforova et al., "BRAF mutations in thyroid tumors are restricted to papillary carcinomas and anaplastic or poorly differentiated carcinomas arising from papillary carcinomas" J Clin Endocrinol Metab, 88, 5399-404, 2003.

Paez et al., "EGFR mutations in lung cancer: correlation with clinical response to gefitinib therapy." Science, 2004, 304, 1497-500.

Pavey et al., "Microarray expression profiling in melanoma reveals a BRAF mutation signature" Oncogene, 2004, 23, 4060-7.

Rabes et al., "Pattern of radiation-induced RET and NTRK1 rearrangements in 191 post-chernobyl papillary thyroid carcinomas: biological, phenotypic, and clinical implications." Clin Cancer Res, 2000, 6, 1093-103.

Rosty et al., "Overexpression of Si 00A4 in pancreatic ductal adenocarcinomas is associated with poor differentiation and DNA hypomethylation." 2002 Am. J. Pathol. 160 45-50.

Santoro et al., "Ret oncogene activation in human thyroid neoplasms is restricted to the papillary cancer subtype" J Clin Invest, 1992, 89, 1517-22.

Sawyers, "Opportunities and challenges in the development of kinase inhibitor therapy for cancer." Genes Dev, 2003, 17, 2998-3010.

Schaefer et al., "Expression profiling of t(12;22) positive clear cell sarcoma of soft tissue cell lines reveals characteristic up-regulation of potential new marker genes including ERBB3." Cancer Res, 2004, 64, 3395-405.

Schwartz et al., "Gene expression in ovarian cancer reflects both morphology and biological behavior, distinguishing clear cell from other poor-prognosis ovarian carcinomas." Cancer Res, 2002, 62, 4722-9.

Segev et al., "Molecular pathogenesis of thyroid cancer" Surg Oncol, 2003, 12, 69-90.

Singer et al.,"Mutations in BRAF and KRAS characterize the development of low-grade ovarian serous carcinoma" J Natl Cancer Inst, 2003, 95, 484-6.

Soares et al., "BRAF mutations and RET/PTC rearrangements are alternative events in the etiopathogenesis of PTC." Oncogene, 2003, 22, 4578-80.

Sorlie et al., "Gene expression patterns of breast carcinomas distinguish tumor subclasses with clinical implications" Proc Natl Acad Sci U S A, 2001 98, 10869-74.

Suarez et al., Oncogene, 1988 2(4):403-406.

Wasenius et al., "Hepatocyte growth factor receptor, matrix metalloproteinase-11, tissue inhibitor of metalloproteinase-1, and fibronectin are up-regulated in papillary thyroid carcinoma: a cDNA and tissue microarray study." Clin Cancer Res, 2003, 9, 68-75.

Welsh et al., "Analysis of gene expression profiles in normal and neoplastic ovarian tissue samples identifies candidate molecular markers of epithelial ovarian cancer" 2001 Proc. Natl. Acad. Sci. 98 1176-1181.

Wilhelm et al., "BAY 43-9006 exhibits broad spectrum oral antitumor activity and targets the RAF/MEK/ERK pathway and receptor tyrosine kinases involved in tumor progression and angiogenesis." Cancer Res, 2004, 64, 7099-109.

Yoon et al., "Peroxisome proliferator-activated receptor gamma target gene encoding a novel angiopoietin-related protein associated with adipose differentiation" Mol Cell Biol 2000; 20:5343-9.

Zhu et al., "Molecular profile and clinical-pathologic features of the follicular variant of papillary thyroid carcinoma. An unusually high prevalence of ras mutations." Am J Clin Pathol, 2003, 120, 71-7.

* cited by examiner

EXPRESSION PROFILE OF THYROID CANCER

This application claims priority to provisional patent application Ser. No. 60/725,389, filed Oct. 11, 2005, which is herein incorporated by reference in its entirety.

This invention was made with government support under DK58771, DK20572, CA88041, and CA 46592 awarded by National Institutes of Health. The government has certain rights in the invention.

FIELD OF THE INVENTION

The present invention relates to compositions and methods for cancer diagnostics, including but not limited to, cancer markers. In particular, the present invention provides gene expression profiles associated with thyroid cancers. The present invention further provides novel markers useful for the diagnosis, characterization, and treatment of thyroid cancers.

BACKGROUND OF THE INVENTION

There are four main types of thyroid cancer papillary, follicular, medullary, and anaplastic. Papillary carcinoma (PC) is the most common type of thyroid cancer, representing up to 80% of all malignant thyroid tumors (Hundahl et al., 1998).

Exposure to radiation to the head and neck during infancy or childhood is correlated with an increased risk of thyroid cancer. The cancer may occur as early as 5 years after exposure or may occur 20 or more years later. Goiter or a family history of thyroid disease is also correlated with an increased risk of developing thyroid cancer.

Prognosis depends on the type of thyroid cancer, whether it is in the thyroid only or has spread to other parts of the body (stage), and the patient's age and overall health. The prognosis is better for patients younger than 40 years who have cancer that has not spread beyond the thyroid.

The majority of PCs are not life threatening and are effectively treated with thyroidectomy followed by radioactive iodine ablation (DeGroot et al., 1990). However, a minority of PCs recur and cause significant morbidity (Hundahl et al., 1998; LiVolsi, 1996). Furthermore, an even smaller minority of PCs undergo progression from well-differentiated carcinoma to either poorly- or undifferentiated carcinoma, an event associated with marked reduction in survival (Giuffrida & Gharib, 2000). What are needed are improved methods for the early diagnosis and treatment of thyroid cancer.

SUMMARY OF THE INVENTION

The present invention relates to compositions and methods for cancer diagnostics, including but not limited to, cancer markers. In particular, the present invention provides gene expression profiles associated with thyroid cancers. The present invention further provides novel markers useful for the diagnosis, characterization, and treatment of thyroid cancers.

Accordingly, in some embodiments, the present invention provides diagnostic methods and kits for diagnosing and characterizing thyroid cancer (e.g. into sub-types). The present invention further provides methods of screening for compounds that modulate cancer marker expression or function and are thus useful as thyroid cancer therapeutics.

For example, in some embodiments, the present invention provides a method for characterizing thyroid tissue, comprising: providing a thyroid tissue sample from a subject; and detecting the level of expression of kallikrein 10 is the sample. In some embodiments, the detecting the level of expression of kallikrein 10 in the sample comprises detecting the level of expression of kallikrein 10 mRNA (e.g., by exposing the mRNA to a nucleic acid probe complementary to the mRNA or by performing a Q-RT-PCR assay). In other embodiments, the detecting the level of expression of kallikrein 10 comprises detecting the level of expression of a kallikrein 10 polypeptide (e.g., by exposing the polypeptide to an antibody specific to the polypeptide and detecting the binding of the antibody to the polypeptide (e.g., using immunohistochemistry).

In some embodiments, an increased level of expression of the kallikrein 10 gene relative to the level of expression of the kallikrein 10 gene in a non-cancerous control is indicative of thyroid cancer in the sample. In some embodiments, the subject comprises a human subject. In certain embodiments, the sample comprises tumor tissue. In some embodiments, the characterizing the thyroid tissue comprises identifying a type of thyroid cancer in the thyroid tissue (e.g., papillary, follicular, medullary, and anaplastic). In some embodiments, the method further comprises the step of providing a prognosis to the subject (e.g., a risk of developing thyroid cancer or metastatic thyroid cancer). In other embodiments, the method further comprises the step of providing a diagnosis to the subject (e.g., a diagnosis of thyroid cancer or a type of thyroid cancer).

The present invention further provides a kit for characterizing thyroid cancer in a subject, comprising: a reagent capable of specifically detecting the level of expression of kallikrein 10 (e.g., a nucleic acid probe or a antibody specific for a kallikrein 10 mRNA or polypeptide); and instructions for using the kit for characterizing thyroid cancer in the subject. In some embodiments, the instructions comprise instructions required by the United States Food and Drug Administration for use in vitro diagnostic products.

The present invention additionally provides a method of screening compounds, comprising: providing a thyroid cell sample; and one or more test compounds; and contacting the thyroid cell sample with the test compound; and detecting a change in expression of kallikrein 10 in the thyroid cell sample in the presence of the test compound relative to the absence of the test compound. In some embodiments, the cell is in vitro or in vivo.

In additional embodiments, the present invention provides a therapeutic agent for treating thyroid cancer. For example, in some embodiments, the therapeutic agent targets a cancer marker identified herein. In other embodiments, the therapeutic agent is a kinase inhibitor (e.g., gleevac or BAY 43-9006).

The present invention further provides a method for characterizing thyroid tissue, comprising: providing a thyroid tissue sample from a subject; and detecting the level of expression of claudin 1 is the sample. In some embodiments, an increased level of expression of the claudin 1 gene relative to the level of expression of the claudin 1 gene in a non-cancerous control is indicative of papillary carcinoma in the sample.

The present invention additionally provides a method for characterizing thyroid tissue, comprising providing a thyroid tissue sample from a patient and detecting the level of expression of one or more genes including, but not limited to, ARNTL, CHST2, CITED1, CLDN1, CLDN16, CTSH, DPP4, DPP4, DPP4, DTX4, ENTPD1, ENTPD1, EVA1, GALNT7, IGSF1, KLK10, MAP3K1, MET, MYH10, PDE5A, PROS1, RAB27A, SLC34A2, SPOCK2, ARHI, DAF, EFA6R, LRP4, NAB2 NELL2, QPCT, RXRG, SARG, SCEL, SDC4, SH2D1A, SLC27A6, TGFA, TIAM1, ALOX5, AMIGO2, BID, C14orf78, C6orf32, CaMKIINalpha, CARD4, CDH3, CHI3L1, CLDN10, CTSC, CTSS, CYP1B1, DCSTAMP, DUSP4, DUSP6, EFA6R, EPS8, FLJ11259, FXYD5, GALE, GALNACT-2, GJB3, HMGA2, ICAM1, IL1RAP, KCNJ2, KCNN4, KIAA0746, KRT15, KRT19, LAMB3, MAP17, MDK, MET, MVP, NAB2, NRIP1, PDLIM4, PHLDA2, PLAU, PLP2, PLXNC1, PLXNC1, PLXNC1, PTPRE, RAB27A, RAB27A, SERPINA1, SFN, TACSTD2, TBC1D2, TIMP1, TMPRSS4 and TNFRSF12A, MID1, NETO2, TEAD4, ADAMTS5, ANK2, BIA2, BMP2, C11orf8, CLCNKA, COPZ2, DEPDC6, DSCR1L1, FHL1, FLJ13842, FLJ20605, FLJ20920, GCAT, GSTM3, IQGAP2, KLHL3, LOC283445, MATN2, MID1, NCAM1, OGDHL, PIP3-E, PPARGC1A, RAP1GA1, RGS16, SLC4A4, SNTA1, SOD3 and TPO. In some embodiments, altered expression of one of the genes relative to the level of expression in normal thyroid is indicative of papillary thyroid cancer in the subject.

The present invention further provides a method for characterizing thyroid tissue, comprising: providing a thyroid tissue sample from a subject; and detecting the level of expression of one or more of PPARG, ATP10B, C6orf29, CHIA, CNR1, AQP7, ANGPTL4, ENO3, TFPI2, MFAP3L, IGFBP2, FBP1, SLC19A1, FBN2, LEPREL1, RAB15, TNFRSF21, CHRNA7, RASSF4, MYOZ1, CCL14, FGFBP1 REPS2, ACAA1, SCNN1A, ARID5B, MYCL1, GFAP, GPR109B, SSX2, XK, DNASE1, SCNN1B, SLC7A8, S100A5, APBB2, DHCR24, SLC39A8, FAM59A, ANKS1, CMKOR1, GENX-3414, FAT2, PLS1, HIC2, GRK5, RASL11B, FDFT1, DECR2, SSX1, ITPR1, SSX3, PMP22, C2orf31, RSU1, PTTG1, ENO2, SALL1, FLJ11196, MAN1C1, PLEKHB1, PTTG3, CUEDC1, MXI1, CHST5, C7orf32, CHPT1, or EPHB2. In some embodiments, altered expression of one of the genes relative to the level of expression in normal thyroid is indicative of follicular thyroid cancer in the subject.

GENERAL DESCRIPTION

Figure 1:
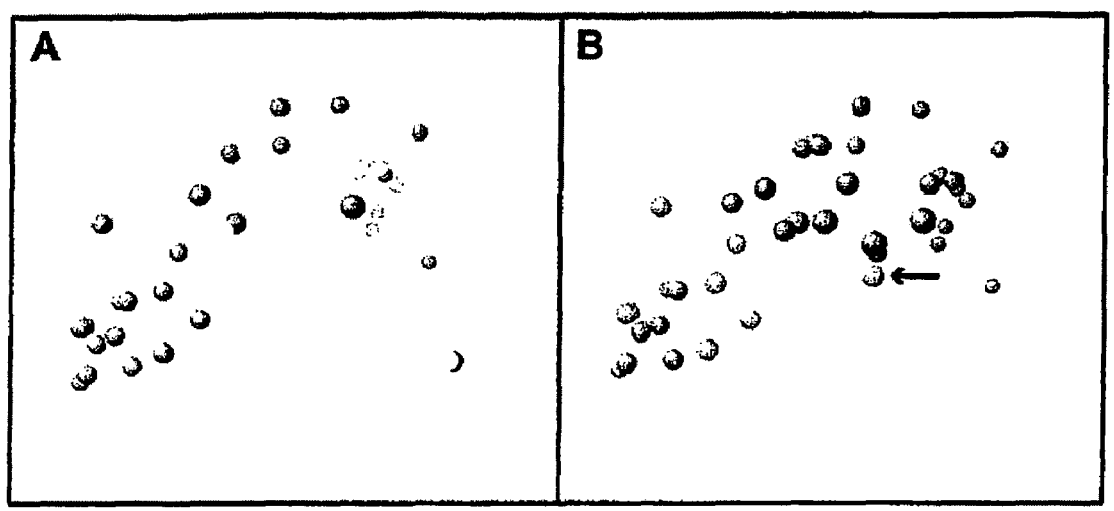
FIGS. 1A and B show principal component analysis of expression profiling data and morphology and mutational status.

Gene expression profiles provide important information about the molecular characteristics of cancers and can be utilized to distinguish closely related cancer subtypes (Welsh et al., Proc. Natl. Acad. Sci. U.S.A, 98: 1176-1181, 2001; Califano et al., Proc. Int. Conf. Intell. Syst. Mol. Biol., 8: 75-85, 2000). Gene profiling can also be used to develop candidate biomarkers (Rosty et al., Am. J. Pathol., 160: 45-50, 2002) and to identify groups of genes involved in specific functional aspects of tumor biology (Gutgemann et al., Arch. Dermatol. Res., 293: 283-290, 2001).

The etiology of PC is incompletely understood despite recent advancements (for reviews, see Bongarzone & Pierotti, Tumori, 89, 514-6, 2003; Fagin, Endocrinology, 143, 2025-8, 2002; Moretti et al., Baillieres Best Pract Res Clin Endocrinol Metab, 14, 517-39, 2000; Segev et al., Surg Oncol, 12, 69-90, 2003). Activating mutations of several genes in the RET/RAS/BRAF/MAPK signal transduction pathway have been identified in the majority of PCs. Specifically, mutations have been identified in the RAS gene family (Bongarzone et al., Oncogene, 4, 1457-62, 1989; Capella et al., Diagn Mol Pathol, 5, 45-52, 1996; Ezzat et al., Thyroid, 6, 409-16, 1996; Karga et al., J Clin Endocrinol Metab, 73, 832-6 1991; Namba et al., Mol Endocrinol, 4, 1474-9 1990; Suarez et al., Oncogene, 22, 4578-80, 1988) and in one member of the RAF kinase family, BRAF (Cohen et al., J Natl Cancer Inst, 95, 625-7, 2003; Kimura et al., Cancer Res, 63, 1454-7, 2003; Nikiforova et al., J Clin Endocrinol Metab, 88, 5399-404, 2003; Soares et al., Oncogene, 22, 4578-80, 2003). Furthermore, PCs contain the well-characterized RET/PTC rearrangements with variable frequency (Santoro et al., J Clin Invest, 89, 1517-22, 1992), in part dependent on geographic factors and radiation exposure (Bounacer et al., Oncogene, 15, 1263-73, 1997; Rabes et al., Clin Cancer Res, 6, 1093-103, 2000). These 3 mutation groups appear to be mutually exclusive (Kimura et al., Cancer Res, 63, 1454-7, 2003; Soares et al., 2003, supra) and are thought to be functionally similar (Kimura et al., 2003, supra). These mutations are believed to be among the earliest initiating mutations in PC, and are followed by additional mutations, such as loss of tumor suppressor genes such as p53 (Dobashi et al., Diagn Mol Pathol, 3, 9-14, 1994; Donghi et al., J Clin Invest, 91, 1753-60, 1993) and PTEN (Frisk et al., Genes Chromosomes Cancer, 35, 74-80, 2002), that correspond to and facilitate the progression towards poorly-differentiated and undifferentiated carcinoma.

Experiments conducted during the course of development of the present invention combined transcriptional expression profiles of 51 PCs with their morphology and RET/PTC, BRAF and RAS mutational status, and thereby demonstrated relationships between gene expression and morphology, and gene expression and mutation. These results refine the classification of PC and improve understanding of its pathobiology.

The finding that gene expression in a tumor reflects its morphology is not unexpected and is also consistent with the literature on a variety of tumor types (Schwartz et al., Cancer Res, 62, 4722-9, 2002), including other endocrine organs (Giordano et al., Am J Pathol, 162, 521-31, 2003). Strong relationships between gene expression and mutation have not been observed in many solid tumor types, with the exception of tumors with dominant activating mutations, such as sarcomas with KIT mutations (Allander et al., Cancer Res, 61, 8624-8, 2001) or characteristic translocations (Schaefer et al., Cancer Res, 64, 3395-405, 2004), melanomas with BRAF mutations (Pavey et al., Oncogene, 23, 4060-7, 2004), hereditary breast (Hedenfalk et al., N Engl J Med, 344, 539-48, 2001) and ovarian carcinoma (Jazaeri et al., J Natl Cancer Inst, 94, 990-1000, 2002), and breast carcinomas that overexpress ERBB2 (Bertucci et al., Oncogene, 23, 2564-75, 2004) or have mutated TP53 (Sorlie et al., Proc Natl Acad Sci USA, 98, 10869-74, 2001). A KRAS2 expression signature of lung adenocarcinomas, not apparent from human tumors alone, was recently derived by combining expression profiles of human and mouse tumors (Sweet-Cordero et al., Nat Genet, 37, 48-55, 2005).

The present invention is not limited to a particular mechanism. Indeed, an understanding of the mechanism is not necessary to practice the present invention. Nonetheless, it is contemplated that the finding of a strong, reproducible relationship between mutation and gene expression in PC indicates that each of these three genetic events likely occur early in tumorigenesis and influence the evolution of the subsequent events, resulting in a persistent and distinct pattern of abnormal gene expression. These findings provide the molecular basis for the development of specific inhibitors for each of these genes and predict their success on blocking the pathways that are central for each tumor development.

The results of experiments conducted during the course of development of the present invention suggest that constitutive activation of one of the components of the RET/RAS/BRAF/MAPK pathway is an event common to all PCs. Furthermore, the strong relationship between gene expression and genotype indicates that mutations affecting this pathway are the predominant source of gene expression variation and suggests that they represent the earliest mutational events occurring in PC. This is supported by findings of RET/PTC rearrangements in papillary microcarcinomas, PCs of less than 1 cm in size (Viglietto et al., Oncogene, 11, 1207-10, 1995). In addition, the absence of a spectrum of dysplasia in well-differentiated PC, in contrast to other epithelial tumor types such as colon carcinoma, suggest that PCs are the morphologic manifestation of single dominant activating mutations. Borderline serous tumors of the ovary share morphologic and molecular features with PC, as each have papillary architectures and a high frequency of BRAF and RAS mutations (Singer et al., J Natl Cancer Inst, 95, 484-6, 2003). Consistent with the PC model, BRAF and RAS mutation are believed to be early events in the development of these tumors (Ho et al., Cancer Res, 64, 6915-8, 2004).

One aspect of the present invention is the ability to define mutation specific gene expression profiles for the RET/PTC, RAS and BRAF oncogenes, which encode effectors residing along the same MAPK signaling pathway. The present invention is not limited to a particular mechanism. Indeed, an understanding of the mechanism is not necessary to practice the present invention. Nonetheless, it is contemplated that the finding that these mutations are associated with distinct sets of signaling consequences suggests that (1) they are able to signal through additional, alternative pathways, and (2) may confer tumors with discrete mutation-specific phenotypical and biological features. First, PCs with BRAF mutations have been reported to follow a more aggressive clinical course (Begum et al., Mod Pathol, 17, 1359-63, 2004; Nikiforova et al., J Clin Endocrinol Metab, 88, 5399-404, 2003). Second, PCs with the follicular architecture tend to have RAS mutations (De Micco, Am J Clin Pathol, 120, 803, 2003; Zhu et al., Am J Clin Pathol, 120, 71-7, 2003), a finding confirmed by this study. Finally, recent cell culture experiments demonstrated that RET/PTC3 mutants signaled preferentially through PI3 kinase compared to MAPK (Miyagi et al., Mol Carcinog, 41, 98-107, 2004). In addition, several of the mutation-specific differentially expressed genes in PC have roles in signal transduction, such as VAV3, ERBB3, MET, DAPP1, and DUSP6. VAV3 is a member of the VAV oncogene family and is involved in phosphoinositide 3-kinase (PI3K) signaling and subsequent akt activation. Its preferential expression in the PCs with RET/PTC and RAS mutations is consistent with the RET/PTC3 cell line data and provides additional evidence these PCs signal more through PI3K than MAPK pathways.

The MET oncogene has been shown to be expressed in PC, especially the TC variant of PC (Nardone et al., Cancer, 98, 1386-93, 2003), and is thought to have a role in its pathogenesis (Ruco et al., J Pathol, 194, 4-8, 2001). Experiments conducted during the course of development of the present invention confirms increased MET expression in PC, and show that this event may be mutation specific. One MET probe set is preferentially expressed in BRAF mutants, while another is preferentially expressed in BRAF and RET/PTC mutants. These findings suggest the possibility of mutations specific alternative splicing, gene rearrangements and partial gene deletions. TIMP1, which is also known to be expressed in PC (Hawthorn et al., Head Neck, 26, 1069-83, 2004b; Huang et al., Proc Natl Acad Sci USA, 98, 15044-9, 2001; Wasenius et al., Clin Cancer Res, 9, 68-75, 2003), is preferentially expressed in RET/PTC and BRAF mutant groups. Several of the mutation-specific differentially expressed genes are known to participate in regulation of the immune response, including TM7SF4 (also DCSTAMP), CLECSF2, STAT1, and LY75. The identification of TM7SF4 as the one of the most preferentially expressed genes in the PCs with BRAF mutations has implications for the immunologic aspects of PC. TM7SF4 is a transmembrane protein expressed in dendritic cells and has a role in antigen processing and initiation of the immune response. Its expression profile, suggests this mutation has a role in initiating an immune response in PC (Baker, J Clin Endocrinol Metab, 80, 3419-20, 1995; Batistatou et al., Endocr Pathol, 13, 111-5, 2002; Juhaszi & Farid, J Clin Endocrinol Metab, 81, 4175-6, 1996).

While RET/PTC rearrangements are unique to PC, mutations of BRAF and the RAS gene family are among the most common types in cancer. Gene expression signatures of melanoma with BRAF mutations compared to melanomas with NRAS mutations have been reported (Pavey et al., Oncogene, 23, 4060-7, 2004). There is little overlap between the PC and melanoma BRAF signatures, suggesting that transcriptional consequences of BRAF mutation may be cell type specific.

Cancers can be broadly divided into 2 categories related to their genotype: those with dominant activating mutations in a relatively stable genomic background and those with multiple activating and loss of tumor suppressor gene mutations in a complex genetic background. Tumors with dominant activating mutations include many of the leukemias and lymphomas, as well as many of the sarcomas. Tumors with complex mutational spectra include most of the common epithelial tumors, such as lung and colon carcinoma. The clear relationship between gene expression profiles and mutation in the present invention suggests that PC fits better within the genetically simple group. Balanced translocations occur in some well differentiated thyroid carcinomas, similar to the situation in hematopoetic malignancies and sarcomas. This observation has clear therapeutic implications, as genetically simple tumors with dominant activating mutations are proving to be more susceptible to targeted molecular therapies (Dancey, Cancer Cell, 5, 411-5, 2004; Lynch et al., N Engl J Med, 35, 2129-39, 2004; Paez et al., Science, 304, 1497-500, 2004).

The finding and validation of reduced TPO expression in BRAF mutant PCs has clinical significance. As TPO plays a vital role in the synthesis of thyroid hormone, it is contemplated that BRAF mutant tumors will display less radioiodine uptake, and thus be less responsive to radioiodine therapy. BRAF mutant tumors are associated with a worse prognosis (Begum et al., Mod Pathol, 17, 1359-63, 2004; Nikiforova et al., J Clin Endocrinol Metab, 88, 5399-404, 2003). Kinase inhibitors, such as imatinib mesylate (GLEEVE® kinase inhibitor), have been shown to be effective in a variety of tumor types and are rapidly becoming accepted as cancer therapeutics (Sawyers, Genes Dev, 17, 2998-3010, 2003). BAY 43-9006 is a novel investigational cancer therapeutic that potently inhibits the serine/theronine kinases RAF-1 and wild-type and V600E mutant BRAF, as well as several receptor tyrosine kinases (Karasarides et al., Oncogene, 23, 6292-8, 2004; Lowinger et al., Curr Pharm Des, 8, 2269-78, 2002; Lyons et al., Endocr Relat Cancer, 8, 219-25, 2001; Wilhelm et al., Cancer Res, 64, 7099-109, 2004). In some embodiments, the present invention provides methods of treating thyroid cancer utilizing RAF kinase inhibitors such as BAY 43-9006. PCs with RET/PTC3 translocations signal preferentially through the PI3 kinase signaling pathway, rather than the RAS/RAF/MEK/ERK pathway.

Experiments conducted during the course of development of the present invention using transcriptional profiles of 51 PCs generated using oligonucleotide DNA microarrays defined 3 main groups of PC that closely correlate with the presence of BRAF, RET/PTC and RAS mutations and also with tumor morphology. These findings indicate that mutational status is the primary determinant of gene expression variation within these tumors, predicting success for therapies designed to prevent the consequences of these specific mutations. Accordingly, in some embodiments, the present invention provides diagnostic and therapeutic markers for thyroid cancer.

Further experiments conducted during the course of development of the present invention identified genes differentially expressed in follicular carcinoma (See e.g., Example 4).

DEFINITIONS

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "characterizing thyroid tissue in a subject" refers to the identification of one or more properties of a thyroid tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. Cancer marker expression may be characterized using any suitable method, including but not limited to, those described herein.

As used herein, the term "a reagent that specifically detects expression levels" refers to reagents used to detect the expression of one or more genes (e.g., including but not limited to, the cancer markers of the present invention). Examples of suitable reagents include, but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous thyroid control" refers to measuring the level of expression of a gene (e.g., the level of mRNA or protein) relative to the level in a non-cancerous thyroid control sample. Gene expression can be measured using any suitable method, including but not limited to, those described herein.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "detecting a change in gene expression (e.g., a change in kallikrein 10 expression) in the thyroid cell sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in the Examples below.

As used herein, the term "instructions for using said kit for detecting cancer in said subject" includes instructions for using the reagents contained in the kit for the detection and characterization of cancer in a sample from a subject.

As used herein, the term "thyroid cancer expression profile map" refers to a presentation of expression levels of genes in a particular type of thyroid tissue (e.g., primary, metastatic, a specific type of thyroid cancer (e.g., papillary carcinoma) and pre-cancerous thyroid tissues). The map may be presented as a graphical representation (e.g., on paper or on a computer screen), a physical representation (e.g., a gel or array) or a digital representation stored in computer memory. Each map corresponds to a particular type of thyroid tissue (e.g., primary, metastatic, and pre-cancerous) and thus provides a template for comparison to a patient sample. In preferred embodiments, maps are generated from pooled samples comprising tissue samples from a plurality of patients with the same type of tissue.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g. the presence or absence of cancerous cells). An initial diagnosis does not include information about the stage of the cancer or the prognosis.

As used herein, the term "biopsy tissue" refers to a sample of tissue (e.g., thyroid tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy- N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules.

For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5 X SSPE (43.8 g/l NaCl, 6.9 g/l NaH$_2$PO$_4$H$_2$O and 1.85 g/l EDTA, pH adjusted to 7.4 with NaOH), 0.5% SDS, 5X Denhardt's reagent and 100 µg/ml denatured salmon sperm DNA followed by washing in a solution comprising 0.1X SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5X SSPE (43.8 g/l NaCl, 6.9 g/l NaH$_2$PO$_4$H$_2$O and 1.85 g/l EDTA, pH adjusted to 7.4 with NaOH), 0.5% SDS, 5X Denhardt's reagent and 100 µg/ml denatured salmon sperm DNA followed by washing in a solution comprising 1.0X SSPE, 1.0% SDS at 42° C. when a probe of about 500 nucleotides in length is employed.

"Low stringency conditions" comprise conditions equivalent to binding or hybridization at 42° C. in a solution consisting of 5X SSPE (43.8 g/l NaCl, 6.9 g/l NaH$_2$PO$_4$H$_2$O and 1.85 g/l EDTA, pH adjusted to 7.4 with NaOH), 0.1% SDS, 5X Denhardt's reagent [50X Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5X SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk—cell lines, the CAD gene that is used in conjunction with CAD-deficient cells and the mammalian hypoxanthine-guanine phosphoribosyl transferase (hprt) gene that is used in conjunction with hprt—cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnostics, including but not limited to, cancer markers. In particular, the present invention provides gene expression profiles associated with thyroid cancers. Accordingly, the present invention provides method of characterizing thyroid tissues, kits for the detection of markers, as well as drug screening and therapeutic applications.

I. Markers for Thyroid Cancer

The present invention provides markers whose expression is specifically altered in cancerous thyroid tissues. Such markers find use in the diagnosis and characterization of thyroid cancer.

A. Identification of Markers

Experiments conducted during the development of the present invention resulted in the identification of genes whose expression level was altered (e.g., increased or decreased) in thyroid cancer. A series of genes were identified that had altered expression in thyroid cancer as compared to normal thyroid (e.g., including, but not limited to, kallikrein 10, claudin 1, and TPO).

Further experiments identified genes differentially expressed in papillary thyroid cancer. Genes found to have increased expression relative to normal thyroid or other types or thyroid cancer include, but are not limited to, ARNTL, CHST2, CITED1, CLDN1, CLDN16, CTSH, DPP4, DPP4, DPP4, DTX4, ENTPD1, ENTPD1, EVA1, GALNT7, IGSF1, KLK10, MAP3K1, MET, MYH10, PDE5A, PROS1, RAB27A, SLC34A2, SPOCK2, ARHI, DAF, EFA6R, LRP4, NAB2 NELL2, QPCT, RXRG, SARG, SCEL, SDC4, SH2D1A, SLC27A6, TGFA, TIAM1, ALOX5, AMIGO2, BID, C14orf78, C6orf32, CaMKIINalpha, CARD4, CDH3, CHI3L1, CLDN10, CTSC, CTSS, CYP1B1, DCSTAMP, DUSP4, DUSP6, EFA6R, EPS8, FLJ11259, FXYD5, GALE, GALNACT-2, GJB3, HMGA2, ICAM1, IL1RAP, KCNJ2, KCNN4, KIAA0746, KRT15, KRT19, LAMB3, MAP17, MDK, MET, MVP, NAB2, NRIP1, PDLIM4, PHLDA2, PLAU, PLP2, PLXNC1, PLXNC1, PLXNC1, PTPRE, RAB27A, RAB27A, SERPINA1, SFN, TACSTD2, TBC1D2, TIMP1, TMPRSS4 and TNFRSF12A. Genes found to have decreased expression relative to normal thyroid or other types or thyroid cancer include, but are not limited to, MID1, NETO2, TEAD4, ADAMTS5, ANK2, BIA2, BMP2, C11orf8, CLCNKA, COPZ2, DEPDC6, DSCR1L1, FHL1, FLJ13842, FLJ20605, FLJ20920, GCAT, GSTM3, IQGAP2, KLHL3, LOC283445, MATN2, MID1, NCAM1, OGDHL, PIP3-E, PPARGC1A, RAP1GA1, RGS16, SLC4A4, SNTA1, SOD3 and TPO.

In particular, additional experiments demonstrated that claudin 1 was preferentially expressed in papillary thyroid carcinoma compared to all the other types.

Yet other experiments identified genes differentially expressed in follicular thyroid cancer. Differentially expressed genes include PPARG, ATP10B, C6orf29, CHIA, CNR1, AQP7, ANGPTL4, ENO3, TFPI2, MFAP3L, IGFBP2, FBP1, SLC19A1, FBN2, LEPREL1, RAB15, TNFRSF21, CHRNA7, RASSF4, MYOZ1, CCL14, FGFBP1, REPS2, ACAA1, SCNN1A, ARID5B, MYCL1, GFAP, GPR109B, SSX2, XK, DNASE1, SCNN1B, SLC7A8, S100A5, APBB2, DHCR24, SLC39A8, FAM59A, ANKS1, CMKOR1, GENX-3414, FAT2, PLS1, HIC2, GRK5, RASL11B, FDFT1, DECR2, SSX1, ITPR1, SSX3, PMP22, C2orf31, RSU1, PTTG1, ENO2, SALL1, FLJ11196, MAN1C1, PLEKHB1, PTTG3, CUEDC1, MXI1, CHST5, C7orf32, CHPT1, and EPHB2.

The present invention is not limited to the particular markers disclosed herein. Additional markers differentially expressed in thyroid cancer are contemplated to be within the scope of the present invention.

B. Detection of Markers

In some embodiments, the present invention provides methods for detection of expression of cancer markers (e.g., thyroid cancer markers). In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In preferred embodiments, the presence of a cancer marker is used to provide a prognosis to a subject.

The present invention is not limited to the markers described above. Any suitable marker that correlates with cancer or the progression of cancer may be utilized, including but not limited to, those described in the illustrative examples below (e.g., kallikrein 10, claudin 1, and TPO). Additional markers are also contemplated to be within the scope of the present invention (See e.g., experimental section). Any suitable method may be utilized to identify and characterize cancer markers suitable for use in the methods of the present invention, including but not limited to, those described in the illustrative Examples below. For example, in some embodiments, markers identified as being up or down-regulated in thyroid cancer using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. For example, a panel may include two or more markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and prognosis. Any of the markers described herein may be used in combination with each other or with other known or later identified cancer markers.

In other embodiments, the present invention provides an expression profile map comprising expression profiles of cancers of various stages or prognoses (e.g., likelihood of future metastasis). Such maps can be used for comparison with patient samples. Any suitable method may be utilized, including but not limited to, by computer comparison of digitized data. The comparison data is used to provide diagnoses and/or prognoses to patients.

1. Detection of RNA

In some preferred embodiments, detection of thyroid cancer markers (e.g., including but not limited to, those disclosed herein) is detected by measuring the expression of corresponding mRNA in a tissue sample (e.g., thyroid tissue). mRNA expression may be measured by any suitable method, including but not limited to, those disclosed below.

In some embodiments, RNA is detected by Northern blot analysis. Northern blot analysis involves the separation of RNA and hybridization of a complementary labeled probe.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to an oligonucleotide probe). A variety of hybridization assays using a variety of technologies for hybridization and detection are available. For example, in some embodiments, the TAQMAN® assay (PE Biosystems, Foster City, Calif.; See e.g., U.S. Pat. Nos. 5,962,233 and 5,538,848, each of which is herein incorporated by reference) is utilized. The assay is performed during a PCR reaction. The TAQMAN® assay exploits the 5'-3' exonuclease activity of the AMPLITAQ GOLD® DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD® polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR(RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of cancer markers is detected by measuring the expression of the corresponding protein or polypeptide. Protein expression may be detected by any suitable method. In some embodiments, proteins are detected by immunohistochemistry. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference is utilized.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of metastasis or the presence of cancer) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

4. Kits

In yet other embodiments, the present invention provides kits for the detection and characterization of thyroid cancer. In some embodiments, the kits contain antibodies specific for a cancer marker, in addition to detection reagents and buffers. In other embodiments, the kits contain reagents specific for (e.g., sufficient for) the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

5. In Vivo Imaging

In some embodiments, in vivo imaging techniques are used to visualize the expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention (e.g., thyroid cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m, which does not use chelation with DPTA, is the pretinning method of Crockford et al., (U.S. Pat. No. 4,323,546, herein incorporated by reference).

A preferred method of labeling immunoglobulins with Tc-99m is that described by Wong et al. (int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen-binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

II. Antibodies

The present invention provides isolated antibodies. In preferred embodiments, the present invention provides monoclonal antibodies that specifically bind to an isolated polypeptide comprised of at least five amino acid residues of the cancer markers described herein (e.g., kallikrein 10, claudin 1, and TPO). These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a cancer marker of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for anticancer drugs). The screening methods of the present invention utilize cancer markers identified using the methods of the present invention (e.g., including but not limited to, kallikrein 10, claudin 1, and TPO). For example, in some embodiments, the present invention provides methods of screening for compounds that alter (e.g., increase or decrease) the expression of cancer marker genes. In some embodiments, candidate compounds are antisense agents (e.g., oligonucleotides) directed against cancer markers. See Section IV below for a discussion of antisense therapy. In other embodiments, candidate compounds are antibodies that specifically bind to a cancer marker of the present invention.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a cancer marker protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity. The cell, for example, can be of mammalian origin.

The ability of the test compound to modulate cancer marker binding to a compound, e.g., a cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer markers substrate in a complex. For example, compounds (e.g., substrates) can be labeled with $^{125}$I, $^{35}$S $^{14}$C or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein or biologically active portion thereof is evaluated. Preferred biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FRET binding event can be conveniently measured through standard fluorometric detection means well known in the art (e.g., using a fluorimeter).

In another embodiment, determining the ability of the cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxysuccinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl. 699:499-525 [1997]). Further, fluorescence energy transfer may also be conveniently utilized, as described herein, to detect binding without further purification of the complex from solution.

The assay can include contacting the cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with thyroid cancer or metastatic thyroid cancer; or an animal harboring a xenograft of a thyroid cancer from an animal (e.g., human) or cells from a cancer resulting from metastasis of a thyroid cancer (e.g., to a lymph node, bone, or liver), or cells from a thyroid cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

IV. Cancer Therapies

In some embodiments, the present invention provides therapies for cancer (e.g., thyroid cancer). In some embodiments, therapies target cancer markers (e.g., including but not limited to, kallikrein 10, claudin 1, and TPO). For example, in some embodiments, therapies down-regulate the expression of kallikrein 10 or upregulate the expression of TPO. In other embodiments, therapies target other proteins in related signaling pathways.

A. RNA Interference (RNAi)

In some embodiments, RNAi is utilized to inhibit kallikrein 10 or modulators of TPO function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

B. Antisense Therapies

In some embodiments, the present invention targets the expression of cancer markers. For example, in some embodiments, the present invention employs compositions comprising oligomeric antisense compounds, particularly oligonucleotides (e.g., those identified in the drug screening methods described above), for use in modulating the function of nucleic acid molecules encoding cancer markers of the present invention, ultimately modulating the amount of cancer marker expressed. This is accomplished by providing antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, $CH_2$—N($CH_3$)—N($CH_3$)—$CH_2$—, and —O—N($CH_3$)—$CH_2$—$CH_2$—[wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O(CH$_2$)$_2$ON(CH$_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of cancer markers of the present invention. Examples of genetic manipulation include, but are not limited to, gene knockout (e.g., removing the cancer marker gene from the chromosome using, for example, recombination), expression of antisense constructs with or without inducible promoters, and the like. Delivery of nucleic acid constructs to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target thyroid tumors that express a cancer marker of the present invention (e.g., kallikrein 10, claudin 1 or TPO modulators). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker of the present invention (e.g., kallikrein 10, claudin 1 or TPO modulators), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a cancer marker of the present invention (e.g., kallikrein 10, claudin 1 or TPO modulators). Immunotoxins are conjugates of a specific targeting agent, typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Other Therapeutics

The present invention is not limited to the above-described cancer therapeutics. Additional therapeutics are contemplated including, but not limited to, small molecule therapeutics. For Example, in some embodiments, a kinase inhibitor such as GLEEVEC® kinase inhibitor or BAY 43-9006 is used as a small molecule therapeutic. In other embodiments, small molecule therapeutics identified using the drug screening methods of the present invention are utilized.

E. Pharmaceutical Compositions

The present invention further provides pharmaceutical compositions (e.g., comprising the therapeutic agents described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

V. Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include, but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); and ° C. (degrees Centigrade).

Example 1

Expression Profile of Thyroid Cancer

This example describes the gene expression profiling of thyroid cancer and the identification of cancer markers using gene expression profiling.

A. Materials and Methods

Tumors, Histopathology and RNA Isolation

The majority of tissues used in this study were procured from surgical pathology specimens from the University of Michigan (UM) via the Tissue Procurement Service (TPS). Additional selected tissues were procured from the University of Cincinnati Medical Center (UC) and the Cooperative Human Tissue Network (CHTN). IRB approval was obtained. The 55 thyroid tissues used in this study included 4 normal thyroid (NT) samples and 51 PCs. All PCs were diagnosed using accepted criteria (DeLellis R. A., 2004). To confirm the diagnoses and ensure research tissues were consistent with the final pathologic diagnosis, frozen section slides were reviewed, as were the original permanent sections, when available. Features of the 51 PCs used in this study are shown in Table 1. The PCs from UMHS were unselected except that tumors had to be large enough to have surplus tissue for procurement. Eight of the nine PCs from UC were selected a priori for their known RET/PTC rearrangements to enrich the study for these tumors.

All tissues and RNAs were processed and extracted similarly. Tissues were embedded in OCT embedding medium (Tissue-Tek, Sakura Finetek, Torrence, Calif.), frozen in liquid nitrogen and stored at −80° C. H&E stained frozen sections were examined to select a representative area of tumor for RNA extraction. Single 2-3 mm$^3$ tissue isolates were removed from the selected area of the block and immediately homogenized in the presence of Trizol reagent (Life Technologies, Gaithersburg, Md.) to prepare total RNA according to manufacturer's procedures. RNA samples were further purified using acid phenol extraction and RNEASY® spin columns (Qiagen, Valencia, Calif.) and used to prepare cRNA probes. RNA quality was assessed by 1% agarose gel electrophoresis in the presence of ethidium bromide. RNA samples that did not show intact 18 S and 28 S ribosomal bands were excluded. To acquire profiles of the 55 thyroid samples, RNA was extracted from 78 thyroid samples.

Oligonucleotide Microarray Analysis

This study used commercially available oligonucleotide DNA microarrays (U133A GeneChip, Affymetrix, Santa Clara, Calif.). Preparation of cRNA, hybridization, scanning and image analysis of the arrays were performed according to manufacturer's protocols and as previously described (Giordano et al., 2001). The U133A arrays consist of 22,283 probe-sets with 68 control probe-sets, each representing a transcript. Each probe-set typically consists of 11 perfectly complementary 25 base-long probes (PMs), as well as 11 mismatch probes (MMs) that are identical except for an altered central base. A representative PC (THY074) was selected as the standard and probe-pairs for which the standard had PM-MM<−100 (15,631 probe-pairs) were excluded from further analysis. Trimmed-means for each probeset on each chip were computed as the average of the PM-MMs for a probe-set after discarding the largest and smallest 20% of the PM-MM differences. The standard was scaled to give average trimmed-mean of 1,500 units. A quantile normalization procedure was used to adjust for differences in the probe intensity distribution across different chips. A monotone linear spline was applied to each chip that mapped quantiles 0.01 up to 0.99 (in increments of 0.01) exactly to the corresponding quantiles of the standard. Next, the data from each chip were log-transformed using the log-transform $y=\log(\max(x+50, 0)+50)$.

Genotyping of PC

The PCs were genotyped for their common activating mutations, RET/PTC1 and RET/PTC3, V600E BRAF, and HRAS, NRAS and KRAS, as described below. THY006 was only genotyped for RAS, and THY004 and THY164 were only genotyped for BRAF and RET/PTC.

Detection of BRAF mutations: Detection of V600E BRAF mutation was performed using realtime PCR and fluorescence melting curve analysis (FMCA) from DNA as previously reported (Nikiforova et al., 2003), or from cDNA using primers 5'-CGACAGACTGCACAGG-3' (SEQ ID NO:1) and 5'-TGACTTCTGGTGCCAT-3' (SEQ ID NO:2) and the same probes.

Detection of RET/PTC rearrangements: Two major types of the rearrangement, RET/PTC1 and RET/PTC3, were detected from RNA by RT-PCR with primers flanking the respective fusion point, followed by agarose gel electrophoresis of the PCR products as previously reported (Nikiforova et al., 2002).

Detection of RAS mutations: Point mutations of the RAS gene most commonly found in thyroid cancer, NRAS codon 61, HRAS codon 61, and KRAS codon 12/13, were detected from DNA using PCR and FMCA on LightCycler as previously reported (Zhu et al., 2003).

Fluorescent in situ hybridization (FISH): One PC (THY152) was studied for RET rearrangement using FISH. A 207 kb BAC clone RPC11-351D16 (BACPAC Resources, Children's Hospital Oakland Research Institute; Oakland, Calif.) spanning the entire RET gene was labeled with SpectrumRed-dUTP (Vysis, Abbott Park, Ill., USA) and used as a probe. A BAC clone RP11-481A12 was used as a probe for ELE1, and a contig of two BAC clones (RP11-43543 and RP11-369L1) as a probe for H4. The ELE1 and H4 probes were directly labeled with SpectrumGreen-dUTP using a nick translation kit (Vysis, Abbott Park, Ill., USA). Hybridization was performed on tumor touch-preparations obtained from snap-frozen tissue and fixed in 3:1 methanol/acetic acid as previously described (Ciampi et al., 2005). Microscopy was performed with a Leica TCS 4D confocal microscope with digital image capture.

Mutation Classifier

Software was written to perform leave-one-out cross-validation of a classification scheme that classifies a sample into one of the three possible mutational classes analyzed here. The classifiers use the 40 PCs with known mutations and G genes per group, using the cases G=1,2 30, as detailed in Table 2. Each sample was left out in turn, and the remaining 39 samples analyzed using a 1-way ANOVA model on log-transformed data, which results in p-values for comparing each pair of classes. For each class, those G genes that had at least two-fold higher expression than in the other two classes, and for which the larger of the two p-values for comparing this group to the other two groups was smallest were selected. The left out sample was classified by majority voting among the 5 nearest neighboring samples (also on log-transformed data) for the 3*G genes selected. Redundancy in the probe-sets representing the same Unigene cluster was first eliminated, since otherwise some genes were selected repeatedly. The classifier based on all 40 PCs with known mutations was used to classify the remaining PCs without detected mutations, and it was occasionally necessary to break ties in the majority voting by selecting one of the tied groups that had the closest single sample.

Thyroid Tissue Arrays and Immunohistochemistry

Two thyroid tissue arrays with a total of 106 PC samples were used in this study and consisted exclusively of tissues from the University of Michigan. Thyroid TMA #2 contained 72 cases of primary PC, and Thyroid TMA #3 contained 34 cases of metastatic PC, with eight cases represented on both arrays. Together they represented 98 unique PC tumors. The majority of the PCs in these arrays were independent of the PCs used to generate the transcriptional gene expression data set. Six of the PCs present on the tissue arrays were also used in the DNA microarray analysis. Thus, 92 of the 98 unique PCs contained in these two thyroid tissue arrays constituted an independent set. As described above, BRAF mutational analysis using DNA from paraffin blocks was attempted in all 106 PC samples, and results were obtained in 102 samples. BRAF mutations were detected in 54/102 (53%) of the PCs represented in the tissue arrays.

Immunohistochemistry for thyroid peroxidase (TPO) was performed using a mouse monoclonal antibody (clone MoAb47, DakoCytomation, Carpinteria, Calif.) at a 1:200 dilution following microwave antigen retrieval in citrate buffer for 20 minutes. After incubation for 60 minutes at room temperature, primary anti-TPO antibodies were detected using the LSAB+kit (DakoCytomation, Carpinteria, Calif.).

The TPO stained thyroid tissue arrays were evaluated by light microscopy using a semi-quantitative approach, as follows: no staining, 0; faint staining, 1+; moderate staining, 2+; strong staining, 3+.

B. Results

Mutational Analysis for BRAF, RAS Family Genes and RET/PTC1 and 3 Rearrangements To uncover relationships between gene expression and activating mutations of the RET/RAS/BRAF/MEK/ERK pathway within PC, the mutational status of RAS, RETIPTC and BRAF for all but one of the PCs was determined. RET/PTC translocation status was determined for the two most common translocations, RET/PTC1 and RET/PTC3. The BRAF mutational analysis was restricted to its most common mutation in adult sporadic PCs, BRAFT1799A. Point mutations within the RAS gene family were determined by examining codons 12 and 13 for KRAS and codon 61 of NRAS and HRAS. The results are detailed in Table 1. Among the entire cohort of 51 PCs, 38 were derived from UMHS, 4 from CHTN and nine from UC. Eight of the 9 samples derived from UC were specifically included to enrich the data for RET/PTC mutant PCs, and are thus excluded from the following mutation frequency calculations. The relative frequency for the three mutations among the remaining unselected PCs (two tumors were not RAS genotyped and one additional tumor was not genotyped for RET/PTC or BRAF) was as follows: BRAF 25/41 (61.0%), RET/PTC 1/42 (2.4%), RAS 5/39 (12.8%). Collectively, BRAF, RET/PTC or RAS mutations were identified in 31/42 (73.8%) PCs. There was no overlap between mutations, as each tumor demonstrated no more than one mutation. These mutation frequencies are consistent with other published studies (Kimura et al., 2003; Nikiforov, 2002).

Gene Expression Profiles Identify Three Groups of Papillary Carcinomas that Reflect Morphology and Mutation Principal components analysis (PCA) was used to carry out an unsupervised examination of the relationship between tumor morphology and global gene expression in the papillary carcinomas (PCs). As seen in FIG. 1A, a direct relationship between morphologic subtype of PC and gene expression was clearly observed. The follicular variants (FV) were closely grouped in the PCA plot, and the tall cell (TC) variants were loosely grouped among the remaining classic types (CT). This relationship between morphology and gene expression profile is consistent with other studies of endocrine tumors (Giordano et al., 2003) and, furthermore, can be interpreted as evidence for the biological relevance of the expression profiles. PCA was also used to examine the relationship between mutation type and gene expression in the PCs. Incorporating the BRAF, RET/PTC and RAS mutational status into the PCA plot revealed a strong relationship between mutation and gene expression (FIG. 1B), with PCs with each mutation type closely grouped. Tumors with BRAF V600E mutations displayed either TC or CT morphology, tumors with RET/PTC mutations displayed predominantly the CT morphology and tumors with RAS mutations exclusively displayed the FV morphology. Tumors with no apparent mutation predominantly had the FV morphology. Some of 10 tumors without BRAF, RET/PTC or RAS mutation were grouped close to the known RAS mutant PCs, suggesting they may contain other RAS mutations not tested here or other mutations that are functionally similar to a RAS mutation (see below under Accurate Prediction of PC Mutational Status Using Marker Genes).

Direct comparison of the two PCA plots revealed that mutation was more strongly correlated with gene expression than morphology. Thus, while morphology and mutation were both related to gene expression, mutational status was a better explanation of the variation in gene expression between samples than tumor morphology.

Transcriptional Signatures Associated with BRAF, RET/PTC and RAS Mutations

To identify differentially expressed genes among the three mutational PC groups, a 1-way ANOVA model was fit to the log-transformed data for the three groups of samples and tests for differences between every pair of groups was computed. Fold-changes for each probe-set for every pair of groups were computed by taking the anti-logarithm of the differences in the means of the log-transformed data. In order to estimate the false discovery rates (FDR), identical calculations were performed on 1,000 additional data sets for which the sample labels were randomly permuted. 3,690 and 3,537 probe-sets with $p<0.01$ were obtained when comparing RET/PTC mutants and BRAF mutants to RAS mutants, respectively, and 3,891 probe-sets with $p<0.01$ for BRAF v. RET/PTC mutant samples, this being approximately 20 times as many as obtained for the permuted data sets on average. The number of differences to consider was reduced by selecting for those that yielded $p<0.01$ as well as a fold-change greater than 2 (or less than 0.5) for any group compared to each of the other two groups. This resulted in 132 probe-sets for RET/PTC mutants (100 up, 32 down, FDR 1.1%), 82 probe-sets for BRAF mutants (31 up, 51 down, FDR 0.5%), and 571 probe-set for the RAS mutant group (165 up, 406 down, FDR=1.4%). The 406 probe-sets selected as being reduced in the RAS mutant group are probe-sets that are larger in the two other mutant groups, indicating that many increases in gene expression are common between BRAF and RET/PTC mutant tumors. Subsets of 20 distinct genes with the smallest P values for the probe-sets selected as up in each of the three groups as well as those up in both RET/PTC and BRAF mutant groups were selected.

Among the differentially expressed genes whose increased expression is the direct consequence of the mutation, for example increased RET expression in PCs with RET/PTC rearrangements, as well as genes involved in a variety of biological processes. For example, the most differentially expressed gene in the BRAF mutants is TM7SF4, which is a dendritic cell protein and is likely related to immune response in these tumors.

Accurate Prediction of PC Mutational Status Using Marker Genes

It was then examined whether expression profiles of a few marker genes could predict the mutational status of the PCs. A leave-one-out cross validation approach was used to test the classifier, given the unavailability of an independent testing set. Using the 40 PCs with identified mutations, leave-one-out cross-validation classifiers were performed based on the best G genes increased in each mutant group, as a way of estimating the misclassification rates expected when presented with new samples. Each PC was left out once and then the other 39 were used to select G genes increased in each group in a manner as detailed in Methods. Using G=I, 2 10 always gave correct classification for all 40 PCs, with one exception. THY105, a BRAF mutant, was classified as a RET/PTC mutant when only 2 probe-sets per group were selected. This tumor expressed considerable RET and may be a PC with more than one type of activating mutation. Given the accuracy of the classifier when using PCs with known mutations, the PCs were then analyzed without apparent mutations using a similar approach. Using the G=I, 2 30 gene per group classifier trained on all 40 PC samples, the 11 remaining PCs were classified without know mutations and the results are detailed in Table 2. THY006, the mutational status of which was not determined, was uniformly classified as a BRAF mutant and had the CT morphology consistent with that predicted genotype. THY152 was always classified as a RET/PTC mutant regardless of the number of genes used by the classifier. FISH later demonstrated that this PC contained a RET/PTC rearrangement, illustrating the accuracy of the classifier (see below). Four PCs (THY048, THY049, THY140, and THY185) had FV morphology and were classified exclusively as RAS mutants. Another FV, THY164, was classified as a RAS mutant when G>3 and a BRAF mutant when G<4. THY004 was classified as a RAS mutant for all numbers of genes per class except when 15 genes were used. The remaining three tumors (THY073, THY098, and THY149) were variably classified depending on the numbers of genes per class (see Table 2).

Testing the Accuracy of the Mutational Classifier by Fluorescence In Situ Hybridization Evaluation of a Misclassified Papillary Carcinoma THY152, one of the PCs with no apparent mutation, was studied to test the accuracy of the mutation classifier. This case was located in the PCA plot away from the other PCs with no mutations (FIG. 1B, arrow), and the mutational classifier uniformly predicted it contained a RET/PTC rearrangement (see above). Additional PCR-based testing of THY152 confirmed the absence of RET/PTC1 and RET/PTC3 translocations. Fluorescence in situ hybridization (FISH) technology was used since it has virtually absolute resolution in determining the presence of any type of RET gene rearrangement. A fluorescently-labeled probe spanning the entire RET gene was used so that rearrangement would result in a split of one of two RET signals. The analysis revealed such a split in most of the tumor cells. Two-color hybridization with the RET and either H4 (RET/PTC1 partner) or ELE1 (RET/PTC3 partner) probes revealed two copies of H4 and ELE1, and no juxtaposition between any of them and RET, indicating the presence of a RET rearrangement which is different from these two most common types.

Figure 2:
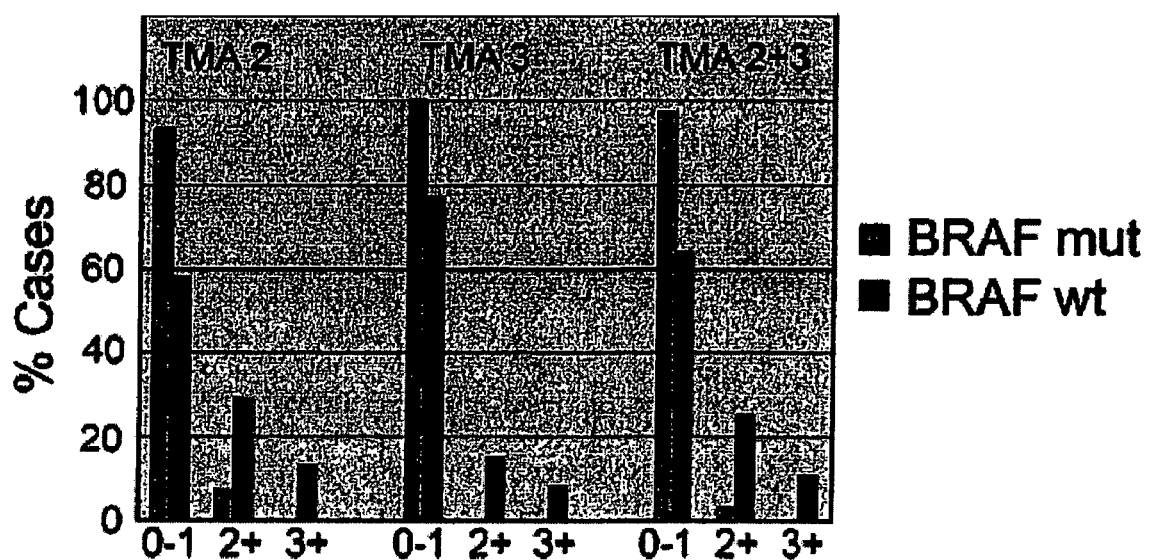
FIG. 2 shows immunohistochemical data for TPO expression.

Testing the BRAF Mutation Gene Expression Signature Using Thyroid Peroxidase Immunohistochemistry in Papillary Carcinoma Tissue Arrays Thyroid peroxidase (TPO) expression is decreased at the transcriptional level in PC (Smanik et al., 1994; Tanaka et al., 1996). The gene expression data concurs, with TPO decreased in the 51 PCs compared to normal thyroid (NT) controls by an average of 18.9-fold (p=0.0007 by two-sided T-test). In the present data set, TPO was not significantly decreased in RAS mutant PCs compared to NTs since 2 of the 5 RAS mutant tumors gave values as large as the NTs. In the present data, BRAF mutant PCs gave the lowest TPO expression values on average, and these were significantly lower than in RAS (p=0.0005, 8.7 fold lower) or RET/PTC mutant PCs (p=0.0009, 5.12 fold lower). TPO gave the largest fold decrease in BRAF compared to RAS and RET/PTC tumors of any gene measured on the present arrays, but was 22nd best as measured by the maximum of these two pvalues. Each of the three groups of mutant PC's had greater than 10 fold ranges for the expression values of TPO and a range of more than 100 fold when combined. It was then investigated whether corresponding protein assays could be used to detect such differences. Immunohistochemistry (IHC) was used to examine TPO protein expression in a independent set of primary and metastatic PCs present in two tissue arrays in which the BRAF mutation status was determined. A 4-point visual interpretation of TPO immunoreactivity resulted in a correlation between TPO protein and BRAF mutational status (FIG. 2A). Representative examples of TPO IHC with BRAF mutational annotation are shown in FIG. 2B.

TABLE 1

Morphologic and Molecular Characteristics of PCs used in this study.

A. Distribution of Morphologic Types of PC

| | Classical Type | Follicular Variant | Tall Cell Variant | Total |
|---|---|---|---|---|
| PC | 26 | 15 | 10 | 51 |

B. Results of PC Genotyping

| | BRAF | RET/PTC | RAS | Negative | Unknown | Total |
|---|---|---|---|---|---|---|
| Selected PCs | 26 | 1 | 5 | 10 | 1 | 43 |
| Unselected PCs | 0 | 8 | 0 | 0 | 0 | 8 |
| All PCs | 26 | 9 | 5 | 10 | 1 | 51 |

TABLE 2

Predicted mutational status for the 11 PCs without apparent mutations. Genes used by the classifier were selected by the other 40 tumors with known mutations from a set of 15,266 probe-sets that were not redundant for the genes (assessed via unigene ID's). For each of the 11 PCs, the predicted mutation based on the number of genes used by the classifier is shown, as well as the morphologic type of each tumor.

| # of genes per class | TC THY004 | FV THY048 | FV THY049 | FV THY073 | FV THY098 | FV THY140 | FV THY149 | CT THY152 | FV THY164 | FV THY185 | CT THY006 |
|---|---|---|---|---|---|---|---|---|---|---|---|
| 1 | RAS | RAS | RAS | RAS | RAS | RAS | RAS | RET/PTC | BRAF | RAS | BRAF |
| 2 | RAS | RAS | RAS | RAS | RAS | RAS | RAS | RET/PTC | BRAF | RAS | BRAF |
| 3 | RAS | RAS | RAS | RAS | RAS | RAS | RET/PTC | RET/PTC | BRAF | RAS | BRAF |
| 4 | RAS | RAS | RAS | RAS | RAS | RAS | BRAF | RET/PTC | RAS | RAS | BRAF |
| 5 | RAS | RAS | RAS | RAS | RET/PTC | RAS | RET/PTC | RET/PTC | RAS | RAS | BRAF |
| 6 | RAS | RAS | RAS | RAS | RET/PTC | RAS | RET/PTC | RET/PTC | RAS | RAS | BRAF |
| 7 | RAS | RAS | RAS | RAS | RET/PTC | RAS | RET/PTC | RET/PTC | RAS | RAS | BRAF |
| 8 | RAS | RAS | RAS | RET/PTC | RET/PTC | RAS | RET/PTC | RET/PTC | RAS | RAS | BRAF |
| 9 | RAS | RAS | RAS | RAS | RET/PTC | RAS | RET/PTC | RET/PTC | RAS | RAS | BRAF |
| 10 | RAS | RAS | RAS | RET/PTC | RET/PTC | RAS | RET/PTC | RET/PTC | RAS | RAS | BRAF |
| 15 | RET/PTC | RAS | RAS | RET/PTC | RAS | RAS | RET/PTC | RET/PTC | RAS | RAS | BRAF |
| 20 | RAS | RAS | RAS | BRAF | RET/PTC | RAS | RET/PTC | RET/PTC | RAS | RAS | BRAF |
| 25 | RAS | RAS | RAS | RET/PTC | RET/PTC | RAS | RET/PTC | RET/PTC | RAS | RAS | BRAF |
| 30 | RAS | RAS | RAS | BRAF | RET/PTC | RAS | RET/PTC | RET/PTC | RAS | RAS | BRAF |

Example 2

Characterization of Thyroid Cancer Markers

Additional expression profiling was performed and identified several genes that were differentially expressed in thyroid cancer. Kallikrein 10 was identified as being upregulated in thyroid cancer. TPO was identified as being down regulated in thyroid cancer.

Example 3

Characterization of Papillary Carcinoma

This Example describes the identification of genes with altered expression in papillary carcinoma, a type of thyroid cancer. The methods used in Example 1 were utilized to identify genes with altered expression in thyroid cancer relative to normal thyroid or other types of thyroid cancer. Genes found to have increased expression relative to normal thyroid or other types or thyroid cancer include, but are not limited to, ARNTL, CHST2, CITED1, CLDN1, CLDN16, CTSH, DPP4, DPP4, DPP4, DTX4, ENTPD1, ENTPD1, EVA1, GALNT7, IGSF1, KLK10, MAP3K1, MET, MYH10, PDE5A, PROS1, RAB27A, SLC34A2, SPOCK2, ARHI, DAF, EFA6R, LRP4, NAB2 NELL2, QPCT, RXRG, SARG, SCEL, SDC4, SH2D1A, SLC27A6, TGFA, TIAM1, ALOX5, AMIGO2, BID, C14orf78, C6orf32, CaMKIINalpha, CARD4, CDH3, CHI3L1, CLDN10, CTSC, CTSS, CYP1B1, DCSTAMP, DUSP4, DUSP6, EFA6R, EPS8, FLJ11259, FXYD5, GALE, GALNACT-2, GJB3, HMGA2, ICAM1, IL1RAP, KCNJ2, KCNN4, KIAA0746, KRT15, KRT19, LAMB3, MAP17, MDK, MET, MVP, NAB2, NRIP1, PDLIM4, PHLDA2, PLAU, PLP2, PLXNC1, PLXNC1, PLXNC1, PTPRE, RAB27A, RAB27A, SERPINA1, SFN, TACSTD2, TBC1D2, TIMP1, TMPRSS4 and TNFRSF12A. Genes found to have decreased expression relative to normal thyroid or other types or thyroid cancer include, but are not limited to, MID1, NETO2, TEAD4, ADAMTS5, ANK2, BIA2, BMP2, C11orf8, CLCNKA, COPZ2, DEPDC6, DSCR1L1, FHL1, FLJ13842, FLJ20605, FLJ20920, GCAT, GSTM3, IQGAP2, KLHL3, LOC283445, MATN2, MID1, NCAM1, OGDHL, PIP3-E, PPARGC1A, RAP1GA1, RGS16, SLC4A4, SNTA1, SOD3 and TPO.

In particular, additional experiments demonstrated that claudin 1 was preferentially expressed in papillary thyroid carcinoma compared to all the other types. Immunohistochemical data confirmed that claudin 1 is preferentially expressed in papillary thyroid carcinoma.

Example 4

Expression Profile of Follicular Thyroid Cancer

A. Materials and Methods

Tumors, Histopathology, and RNA Isolation

A total of 93 unique thyroid samples consisting of 4 normal thyroids and 89 thyroid tumors (7 follicular carcinomas with the PAX8-PPARG translocation, 6 follicular carcinomas without the translocation (including Thy203, described below), 10 follicular adenomas, 8 oncocytic carcinomas, 7 oncocytic adenomas, and 51 papillary carcinoma) were used to generate the gene expression profiles. Cases were derived from the University of Michigan, the University of Cincinnati Medical Center, and the Cooperative Human Tissue Network. The 51 papillary carcinomas and the four normal thyroids were described previously (Giordano et al., Oncogene 2005; 24:6646). All tumors were diagnosed using accepted morphologic criteria. Frozen section slides and original permanent sections were reviewed, when available, to confirm the diagnoses and ensure research tissues were in agreement with the final pathologic diagnosis. All tissues were processed and RNAs were extracted similarly, as previously described (Giordano et al., Am J Pathol 2001; 159:1231).

Microarray Analysis

DNA microarray analysis was done using commercially available oligonucleotide DNA microarrays containing 22,283 probe sets (U133A GeneChip, Affymetrix, Santa Clara, Calif.) as reported (Giordano et al., 2005, supra; Shedden et al., BMC Bioinformatics 2005; 6:26). cRNA preparation and hybridization, and scanning and image analysis of the arrays were done according to protocols of the manufacturer and as previously described (Giordano et al., 2001, supra), as was probe set intensity estimation and normalization. The procedures gave average probe set intensities of approximately 1,500 units, which were log-transformed using log [max(x+50,0)+50]. Estimates of fold changes between groups are the antilogarithms of the differences in means of the log transformed data.

Quantitative Reverse Transcription-PCR and Sequencing

Reverse transcription real-time PCR was done as previously described (Thomas et al., Cancer 2005; 103:830). The probes and labels, shown in Table 3, (SEQ ID NOS: 3-19) were designed using Primer Express (ABI, Foster City, Calif.) and were obtained from Biosearch Technologies (Novato, Calif.). PCR conditions for each primer-probe combination were optimized for time, temperature, and magnesium concentration and done using a SmartCycler (Cepheid, Sunnyvale, Calif.). PCR products were sequenced in both directions by the University of Michigan DNA Sequencing Core.

TABLE 3

| Gene | Direction | Primer sequence |
|---|---|---|
| PPARG | Forward | GGCCAAGGCTTCATGACAA |
|  | Reverse | AACTCAAACTTGGGCTCCATAAAG |
|  | Probe | TAAAGAGCCTGCGAAAGCCTTTTGGTG |
|  | Label | FAM |
| PAX8-PPARG | Forward | AAAGCACCTTCGCACGGATG |
|  | Reverse | ACGGAGCTGATCCCAAAGTTGG |
|  | Probe | None |
|  | Label | SYBR green |
| PGF | Forward | TCCTTGTCCCCCGTGATCT |
|  | Reverse | TGGCCGGAAAGAACAATGTC |
|  | Probe | CCCTCACACTTTGCCATTTGCTTGTACTG |
|  | Label | TAMRA |
| ENO3 | Forward | GGACCGAGAATAAGTCCAAGTTTG |
|  | Reverse | AGCTGCTCCCGCCTTACAC |
|  | Probe | ATGCCATCCTGGGCGTGTCCTTG |
|  | Label | FAM |
| AQP7 | Forward | ACCCTGCCCCACCCTTAC |
|  | Reverse | GGAATGGATGGGATCACAAATAAT |
|  | Probe | TCCATGGCCCTAGAGCACTTCTAAGCAGA |
|  | Label | FAM |
| ANGPTL4 | Forward | CATGGTGCTGGTGCTGTTGT |
|  | Reverse | AGGTTGCTTTTATTCCAAGAACTCTGT |
|  | Probe | CAAGCAGGCGCCAATGGTATCTGG |
|  | Label | FAM |

Tissue Array and Immunohistochemistry

A thyroid tissue array was constructed for validation by immunohistochemistry studies. The four PPFP(+) follicular carcinomas from the University of Michigan were used along with two PPFP(−) follicular carcinomas, four papillary carcinomas, two follicular adenomas, and four normal thyroids. One millimeter-diameter cores were arrayed in duplicate.

Immunohistochemistry was done using a robotic autostainer (DAKO, Carpinteria, Calif.) and standard procedures using the Envision detection system (DAKO). The following antibodies and conditions were used: PPARg (Santa Cruz Biotechnology, Santa Cruz, Calif.), 1:100 dilution, high-pH Tris antigen retrieval, 60 minutes room temperature incubation; enolase 3 (ENO3; BD Transduction Laboratories, San Jose, Calif.), 1:50 dilution, citrate buffer antigen retrieval, 60 minutes room temperature incubation; and aquaporin 7 (AQP7; Abcam, Cambridge, Mass.), 1:800 dilution, citrate buffer antigen retrieval, 30 minutes room temperature incubation.

Cell Culture and Transfection Assays

All cells were maintained at 37° C. with 5% CO2. JEG-3 human choriocarcinoma cells were cultured in Eagle's MEM with 10% fetal bovine serum and penicillin/streptomycin. N2a mouse preneuronal cells were cultured in DMEM with 10% fetal bovine serum and penicillin/streptomycin. Rat FRTL-5 thyroid cells were cultured in F12 Coon's media with 5% fetal bovine serum, six hormone combination (1 mU/mL bovine TSH, 4 ng/mL insulin, 10 ng/mL somatostatin, 5 Ag/mL apotransferrin, 4 mg/mL hydrocortisone, and 10 ng/mL glycyl-L-histidyl-L-lysine acetate; Sigma, St. Louis, Mo.) and penicillin/streptomycin.

Whole thyroid glands were removed from dogs that had been previously anesthetized and exsanguinated as part of an unrelated, institutionally approved study. Thyroid glands were removed within 10 minutes of exsanguination. Glands were trimmed, minced, and primary cultures of thyrocytes were obtained following the method of Uyttersprot et al. (Uyttersprot et al., Mol Cell Endocrinol 1998; 142:35).

The promoters of four genes that, according to the microarray data, were induced specifically in PPFP(+) follicular carcinomas were selected for analysis by transfection. The PCR was used with Accuprime Pfx polymerase (Invitrogen, Carlsbad, Calif.) to amplify human AQP7 bp −2,359 to +90 (the transcription start site is +1), angiopoietin-like protein 4 (ANGPTL4) bp −2,565 to +77, placental growth factor (PGF) bp −2,372 to +34, and ENO3 bp −2,808 to +56. The respective templates for these reactions were human genomic DNA and bacterial artificial chromosomes RP11-886P16, RP11-104F2, and RP5-1050D4. The 5V PCR primers contained an Mlu1 restriction enzyme site and the 3V primers contained either an Xho1 or Sal1 site. The PCR products were digested with the appropriate enzymes and ligated into the Mlu1 and Xho1 sites of pGL3-basic (Promega, Madison, Wis.). All constructs were confirmed by sequencing.

For transfection, cells were plated into 24-well clusters. The day before transfection, the medium was replaced to include charcoal stripped serum. Transfections were done with LipofectAMINE and Plus reagents according to the protocol of the manufacturer (Invitrogen) in serum-free medium, and included 100 ng of the above-described pGL3-based firefly luciferase reporter plasmids, 100 ng transcription factor expression plasmid (PAX8, PPARg, PPFP, or empty vector pCDNA3.1+; Invitrogen), and 0.5 to 1 ng of the internal control Renilla luciferase plasmid pRL-SV40 (Promega). After 3 hours of transfection, an equal volume of culture medium containing 20% charcoal-stripped FCS and penicillin/streptomycin was added to the wells. The next day, the culture medium was replaced with medium containing either 10 Amol/L PPARg agonist ciglitazone (Willson et al., J Med Chem 1996; 39:665) or vehicle ethanol (again with 10% stripped serum) for an additional 24 hours. The cells were lysed and analyzed for firefly and Renilla luciferase activities using the Promega dual luciferase reagents and protocol.

Enriched Feature Tests

A selected set of 977 probe sets were tested for overrepresentation of any Gene Ontology terms, GenMAPP maps using probe set annotation from Affymetrix, as well as pathways defined in the Kyoto Encyclopedia of Genes and Genomes using methods similar to those previously reported (Thy203 was omitted in this analysis; Creighton et al., Genome Biol 2003; 4:R46). The 22,283 U133A GeneChip probe sets were collapsed to 12,44 distinct genes with unambiguous Entrez gene numbers, which reduced the 977 probe sets to 761 genes (460 up, 301 down). Overrepresentation of each annotation term (e.g., membership in a particular pathway) in this set of genes was tested using one-sided Fisher's exact tests. To estimate the false discovery rates for the most significantly enriched terms, the resulting P values were compared with P values obtained from 100 data sets in which the 761 genes were randomly selected.

Bioinformatic Analysis Using Oncomine

The Oncomine data mining platform (Rhodes et al., Neoplasia 2004; 6:1) was used to compare the PPFP(+) and PPFP (−) follicular carcinoma gene expression profiles (including Thy203). Genbank accession IDs corresponding to Affymetrix probe set IDs were downloaded from Netaffx (Affymetrix). Genbank IDs were mapped to Unigene Build 185. A map from Unigene to Entrez Gene ID was downloaded from Entrez Gene. The data set was base 2 log transformed (negative intensity values were removed) and median centered per array, and the SDs were normalized to one per array. Each gene was assessed for differential expression with Student's t test, done using the R statistical computing package. Tests were conducted both as two-sided for differential expression analysis and one-sided for overexpression analysis. To account for multiple hypothesis testing, Q values (estimated false discovery rates) were calculated as follows: $Q=(N \times P)/R$, where P is P value, N is the total number of genes analyzed, and R is the sorted rank of P value.

Gene Set Collection

All identifiers were mapped to Entrez Gene Ids for analysis. The 22,283 probe sets were collapsed to 13,046 distinct Entrez gene IDs. In the case of multiple probe sets per Entrez gene ID, the probe set with the minimum P value was kept. Sets of biologically related genes were collected or derived from a number of external resources; those relevant to the data presented here are as follows: chromosome arm mappings were downloaded from the National Center for Biotechnology Information Map Viewer, protein-protein interaction sets were downloaded from the Human Protein Reference Database, and predicted micro-RNA (miRNA) target genes were downloaded from Pictar.

Gene Set Analysis

Oncomine gene expression signatures were defined as the top 20% of Entrez gene IDs with enough nonnegative values to perform at test, rank-ordered by their P values in each differential expression analysis. This constitutes 12,078 distinct genes, giving 2,415 in the top 20%. The association of a gene expression signature and the gene set was assessed with Fisher's exact test. The false discovery rate was again estimated using Q values, calculated as follows: $Q=(N \times P)/R$, where N is the number of gene sets of a given type tested against each gene expression signature and R is the ascending order rank of the respective P value.

Interactome

Approximately 16,000 known protein-protein interactions were downloaded from the Human Protein Reference Database, a manually curated database of pairs of proteins that have experimental evidence for physical interaction. Oncomine reports pairs of differentially expressed genes that encode proteins with documented protein-protein interactions. Oncomine generates interactome maps for the top 10% of genes rank-ordered by their P values in each differential expression analysis.

B. Results

Figure 3:
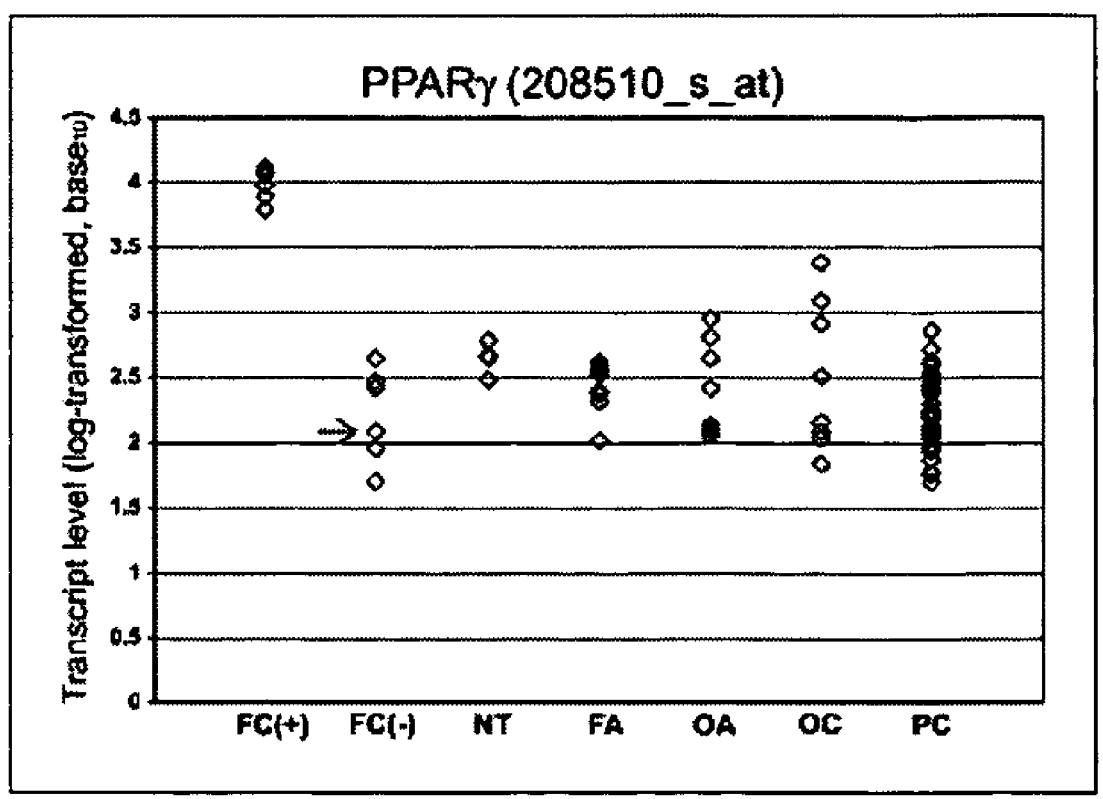
FIG. 3 shows microarray analysis of PPARg expression in benign and malignant thyroid samples.

Gene Expression Profiling Identifies Follicular Carcinomas with the PAX8-PPARG Translocation Experiments were conducted to identify the transcriptional changes that are specific to follicular carcinomas that contain the PAX8-PPARG translocation. For this purpose, gene expression profiles were obtained on 93 thyroid samples consisting of 4 normal thyroids and 89 thyroid tumors (13 follicular carcinomas, 10 follicular adenomas, 8 oncocytic carcinomas, 7 oncocytic adenomas, and 51 papillary carcinomas). It was possible to identify cases with the PAX8-PPARG translocation by examining the microarray data for increased expression of PPARγ (FIG. 3). High PPARγ transcript levels, compared with the other thyroid tumors, were present in seven of the follicular carcinomas. All the follicular patterned tumors (follicular carcinomas, follicular adenomas, oncocytic carcinomas, and oncocytic adenomas) were analyzed by reverse transcription-PCR for the presence of the fusion transcript. The fusion transcript was detected in all seven follicular carcinomas with high PPARγ expression and in only one other sample, a follicular carcinoma (Thy203) that expressed very low levels of PPARγ by microarray (FIG. 3). By reverse transcription real-time PCR, the threshold for detection of the fusion transcript occurred 10 cycles later for Thy203 than for the seven follicular carcinomas with high PPARγ expression, indicating that Thy203 expresses the fusion transcript at approximately 0.1% the level of those seven follicular carcinomas. Further, real-time PCR for the 3V end of PPARγ showed an undetectable level of expression after 40 cycles of amplification (Table 4). Therefore, for analysis, Thy203 was grouped with the PPFP(−) follicular carcinomas. The microarray profile of Thy203 was similar to those of the five other PPFP(−) follicular carcinomas.

TABLE 4

| Tumor | PPARG | PGF | ANGPTL4 | AQP7 | ENO3 |
|---|---|---|---|---|---|
| PPFP(+) FC (n = 7) | 21.2 (3.1) | 24.4 (3.2) | 23.7 (1.5) | 23.8 (1.0) | 25.9 (1.5) |
| All others (n = 70) | 38.6 (4.7) | 29.1 (6.0) | 38.1 (4.7) | 37.4 (4.8) | 33.5 (4.5) |
| All PPFP(−) FC (n = 10) | 40.0 (0.0) | 28.7 (7.1) | 37.4 (5.6) | 36.7 (5.5) | 33.5 (5.2) |
| PPFP(−) FC (n = 6)* | 40 (0.0) | 29.6 (9.2) | 35.6 (6.8) | 38.7 (3.2) | 32.3 (6.0) |
| PPFP(−) FC (n = 4)† | 40.0 (0.0) | 27.4 (2.2) | 40 (0.0) | 33.7 (7.3) | 35.4 (3.7) |
| Thy203 | 40.0 | 27.2 | 40 | 32.2 | 40.0 |
| NT (n = 4) | 36.5 (7.0) | 24.6 (3.4) | 40.0 | 35.4 (5.3) | 33.4 (2.9) |
| FA (n = 14) | 40 (0.0) | 25.9 (4.6) | 38.3 (4.5) | 36.4 (5.2) | 31.3 (4.1) |
| NH (n = 8) | 38.4 (4.7) | 27.9 (5.5) | 40 (0.0) | 40 (0.0) | 35.4 (3.2) |
| OA (n = 7) | 39.6 (1.1) | 34.7 (5.1) | 40 (0.0) | 32.3 (5.7) | 31.6 (3.0) |
| OC (n = 7) | 37.6 (9.7) | 35.8 (5.6) | 38.4 (4.3) | 40 (0.0) | 35.6 (3.5) |
| PC (n = 19) | 38.2 (4.4) | 28.8 (4.5) | 37.4 (5.3) | 39.5 (2.3) | 34.8 (5.0) |

NOTE:
Values in table expressed as mean cycle to threshold (SD). PCR reactions that did not reach threshold by the 40th cycle were assigned a value of 40.
Abbreviations:
FC, follicular carcinoma;
NT, normal thyroid;
FA, follicular adenoma;
OA, oncocytic adenoma;
OC, oncocytic carcinoma;
PC, papillary carcinoma.
*Follicular carcinomas that were used for DNA microarray analysis.
†Follicular carcinomas that were not used in the microarray analysis.

Characterization of Transcript Fusions in the PPFP(+) Follicular Carcinomas and Thy203

PPFP transcripts have been reported to contain PAX8 exons 7, 8, or 9 fused to PPARγ1 exon 1 (Kroll et al., Science 2000; 289:1357). Reverse transcription-PCR using a forward primer in PAX8 exon 7 and a reverse primer in PPARγ1 exon 1 followed by sequencing revealed that six of the seven PPFP (+) follicular carcinomas had transcripts with PAX8 exon 8 fused to PPARγ1 exon 1, and one (Thy150) had PAX8 exon 7 fused to PPARg1 exon 1. Thy203 also showed fusion of PAX8 exon 8 to PPARγ1 exon 1.

Figure 4:
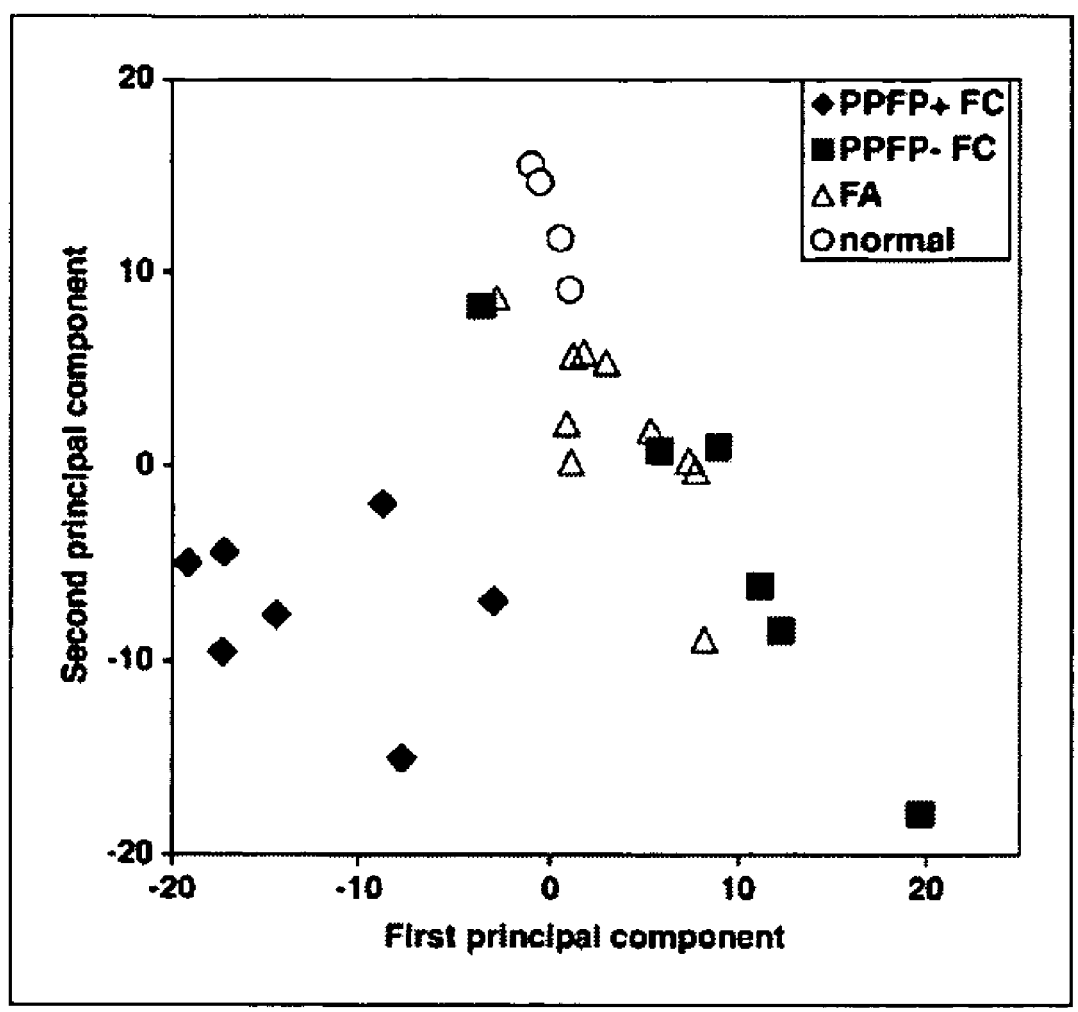
FIG. 4 shows principle component analysis of log-transformed data for all probe sets for PPFP(+) follicular carcinomas (PPFP+FC), PPFP(−) follicular carcinomas (PPFP−FC), follicular adenomas (FA), and normal thyroids.

Gene Expression Among Follicular Patterned Lesions is a Function of the PAX8-PPARG Translocation Principal component analysis was done to examine global differences in gene expression between samples. Principal component analysis of all follicular neoplasms (23 follicular carcinomas and follicular adenomas) revealed significant separation of the PPFP(+) follicular carcinomas from the PPFP(−) follicular carcinomas and the follicular adenomas (FIG. 4). This result indicates that the PAX8-PPARG translocation is the predominant source of the gene expression variation within this set of tumors. Thy203 plotted among the other PPFP(−) follicular carcinomas, providing further support for its inclusion in the PPFP(−) follicular carcinoma group.

Gene Expression Profile of Follicular Carcinomas with the PAX8-PPARG Translocation The most direct way to define the expression profile of follicular carcinomas with the PAX8-PPARG translocation is comparison of a large number of follicular carcinomas with and without the translocation. However, in general, follicular carcinomas are relatively rare thyroid tumors and microarray analysis requires frozen tissue. Thus, only 13 follicular carcinomas were available for analysis. Therefore, all of the data from the various tumor types was used to identify genes with larger (or smaller) mRNA levels in the seven PPFP(+) follicular carcinomas compared with the five PPFP(−) follicular carcinomas without this translocation (Thy203 was omitted), which also were increased (or decreased) compared with non-follicular carcinoma tumor samples and normal tissue. It was asked that two-sample t tests give P<0.01 for the comparison of PPFP(+) follicular carcinomas to PPFP(−) follicular carcinomas, as well as for the comparison of PPFP(+) follicular carcinomas to the set of nonfollicular carcinoma samples. It was further asked that the fold difference between PPFP(+) follicular carcinomas and each of the six groups individually be at least 1.5 and be in the same direction. This selected a set of 322 probe sets, 239 of which had increased values in the PPFP(+) follicular carcinomas. To estimate the false discovery rate for this gene list, the sample labels were permutated 1,000 times, and on average 3.85 qualifying probe sets in the 1,000 resulting data sets were obtained, so the false discovery rate was estimated to be approximately 1.2%. When performing statistical tests for enriched features among sets of genes, it was asked that the P values be <0.05 and the fold changes be at least 1.2. This selected 977 probe sets with an estimated false discovery rate of 11.4%.

Figure 5:
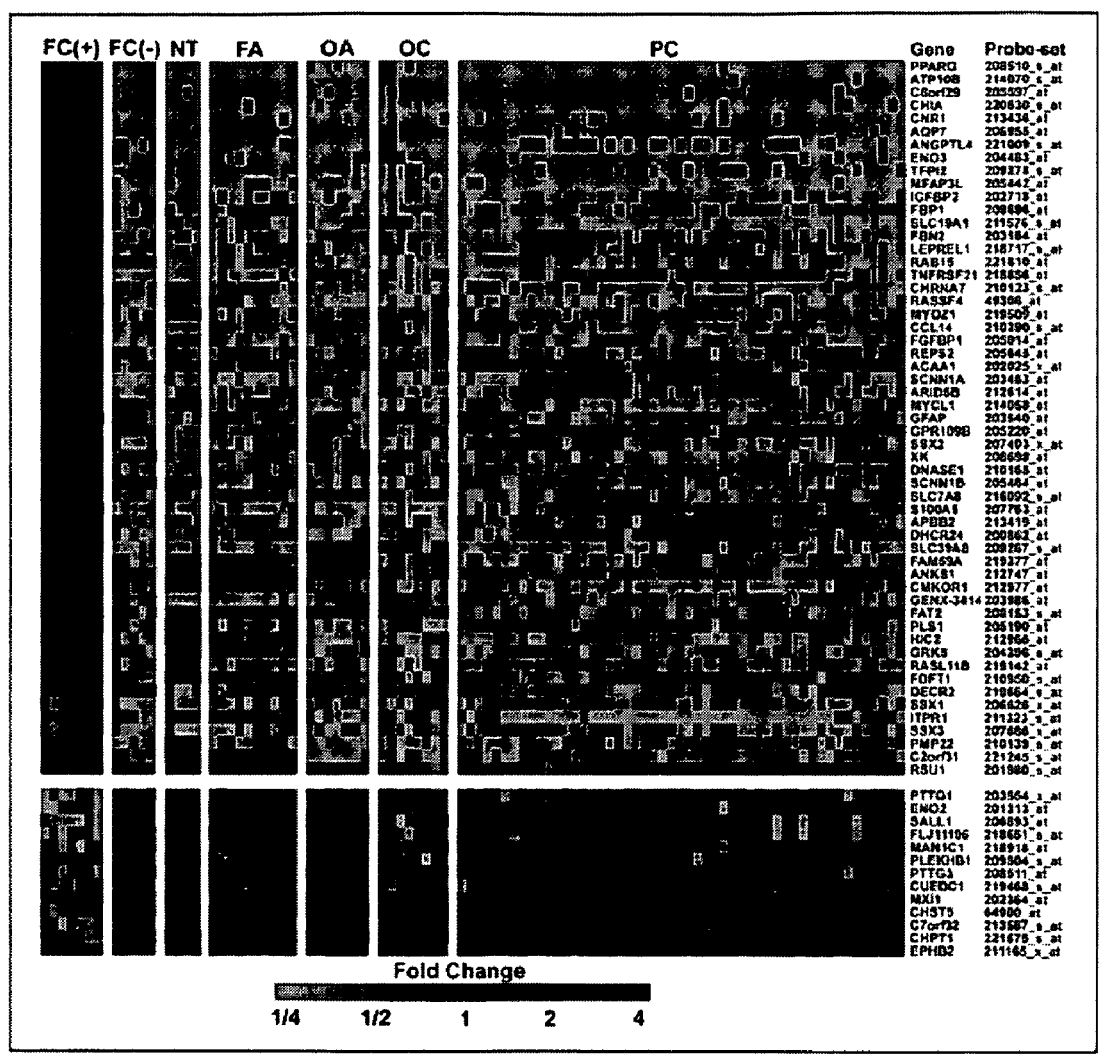
FIG. 5 shows gene expression signature of follicular carcinomas with the PAX8-PPARG translocation.

FIG. 5 shows a smaller subset that qualified under a similar but more stringent selection criteria that required the two P values to be <0.001 and the fold changes be at least 2.0. This selected 80 probe sets (67 up, 13 down) representing 68 distinct genes (55 up, 13 down), and gave an estimated false discovery rate of 0.07% using 1,000 permuted data sets. PPARG is the most differentially expressed gene, but this reflects the expression of PPFP in tumors with the PAX8-PPARG translocation. The expression of several thyrocyte differentiation markers genes (SLC5A5, TG, TPO, and TSHR) between the PPFP(+) follicular carcinomas and the other follicular cohorts were investigated and few significant changes were found.

Genes found to have altered expression include PPARG, ATP10B, C6orf29, CHIA, CNR1, AQP7, ANGPTL4, ENO3, TFPI2, MFAP3L, IGFBP2, FBP1, SLC19A1, FBN2, LEPREL1, RAB15, TNFRSF21, CHRNA7, RASSF4, MYOZ1, CCL14, FGFBP1 REPS2, ACAA1, SCNN1A, ARID5B, MYCL1, GFAP, GPR109B, SSX2, XK, DNASE1, SCNN1B, SLC7A8, S100A5, APBB2, DHCR24, SLC39A8, FAM59A, ANKS1, CMKOR1, GENX-3414, FAT2, PLS1, HIC2, GRK5, RASL11B, FDFT1, DECR2, SSX1, ITPR1, SSX3, PMP22, C2orf31, RSU1, PTTG1, ENO2, SALL1, FLJ11196, MAN1C1, PLEKHB1, PTTG3, CUEDC1, MXI1, CHST5, C7orf32, CHPT1, and EPHB2.

Validation of Select Genes by Reverse Transcription Real-Time PCR

To validate the microarray data, reverse transcription real-time PCR was done using RNA from a set of tumors that partially overlapped with the set used for DNA microarray analysis. PPARG and four additional genes with increased expression in the PPFP(+) follicular carcinomas were selected for validation (ANGPTL4, AQP7, ENO3, and PGF). The results, reported as the number of cycles needed to reach threshold (cycle to threshold, CT), are shown in Table 4 listed by histologic type and translocation status. Overall, the PCR results validate the microarray data, including classification of Thy203 as PPFP(−).

Validation of Select Proteins by Immunohistochemistry

To validate the microarray data at the protein level, immunohistochemistry for PPARγ and two proteins (ENO3 and AQP7) identified in the PPFP(+) signature was done using a thyroid tissue array that contained four PPFP(+) follicular carcinomas as well as a 10 other thyroid tumors (including two PPFP(−) follicular carcinomas) and four normal thyroids. The results confirmed increased protein expression in PPFP (+) follicular carcinomas of PPARγ (four of four, 100%), ENO3 (three of four, 75%), and aquaporin (three of four, 75%) compared with normal thyroid and the other thyroid tumors.

Functional Validation of the Gene Expression Signature by Transient Transfection Assays Two of the genes most strongly induced specifically in the PPFP(+) follicular carcinomas, AQP7 and ANGPTL4, are induced by PPARγ in other tissues (Kishida et al., J Biol Chem 2001; 276:48572; Yoon et al., Mol Cell Biol 2000; 20:5343). The present invention is not limited to a particular mechanism. Indeed, an understanding of the mechanism is not necessary to practice the present invention. Nonetheless, it is contemplated that PPFP induces these genes in a PPARγ-like manner. Therefore, transient transfection was used to compare the abilities of PPFP, PPARγ, and PAX8 to regulate the AQP7 and ANGPTL4 promoters. The promoters from two additional genes induced specifically in the PPFP(+) follicular carcinomas, PGF and ENO3, were also studied. Three different cell lines and primary cultures of dog thyrocytes were transfected to assess whether cell type-specific factors might regulate the response.

Preliminary studies were done to show the functional capacity of the primary dog thyrocyte cultures. The thyrocytes were transfected with a reporter plasmid in which the rat sodium iodide symporter gene upstream enhancer element and 2 kbp proximal promoter direct firefly luciferase expression (NIS-luc), together with a cytomegalovirus-Renilla luciferase internal control plasmid. Exposure to 15 mIU/mL TSH for 24 hours induced NIS-luc 2.3 F 0.09-fold (n=3), indicating that the cells are responsive to TSH. Separate immunohistochemical experiments showed uniformly positive thyroglobulin staining.

Figure 6:
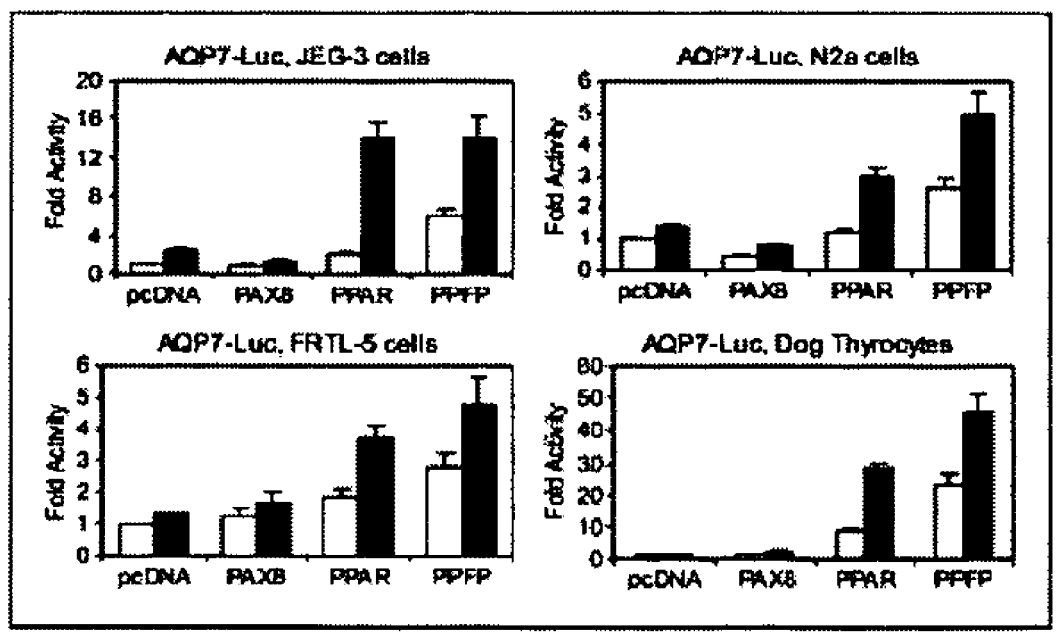
FIG. 6 shows regulation of the AQP7 promoter.
Figure 7:
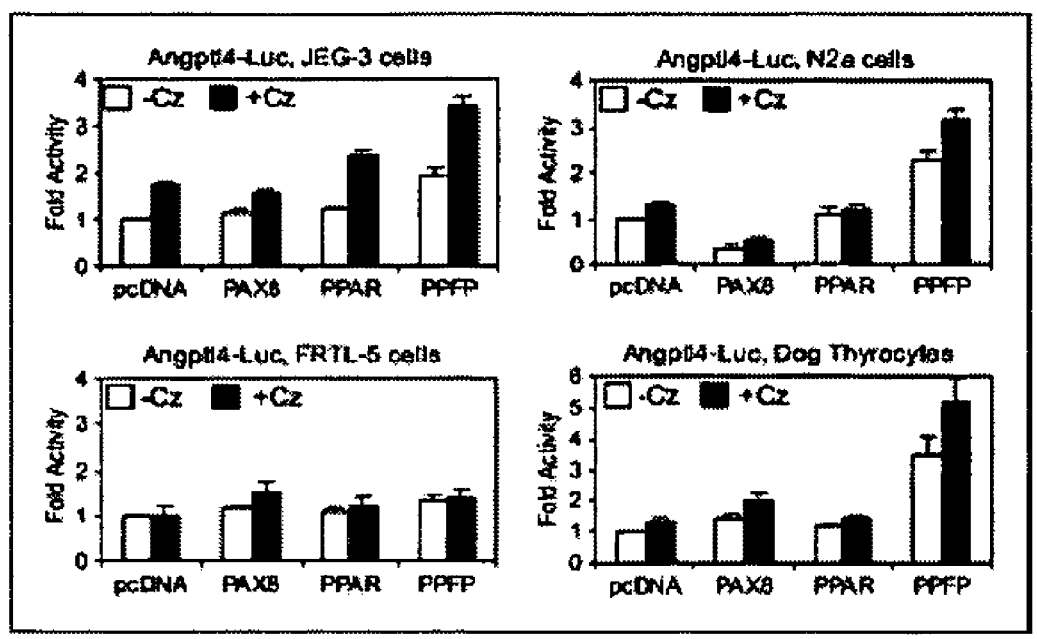
FIG. 7 shows regulation of the ANGPTL4 promoter.

The AQP7 promoter was strongly induced by PPARγ and PPFP, but not by PAX8, in all four cell types (FIG. 6). PPARγ and PPFP showed similar levels of induction in the presence of the PPARγ agonist ciglitazone, although PPFP tended to have stronger ligand-independent activity. For example, in JEG-3 cells, PPARγ induced luciferase 2.1-fold in the absence and 14-fold in the presence of ciglitazone, whereas the inductions with PPFP were 5.9- and 14-fold. Similarly, in primary cultures of dog thyrocytes, PPARγ induced luciferase 8.8-fold in the absence and 29-fold in the presence of ciglitazone, whereas the inductions with PPFP were 23- and 46-fold. The ANGPTL4 promoter was less responsive than AQP7 and the data showed some cell type specificity, but the overall trend was similar with PPFP being at least as active as PPARγ, and PAX8 having no activity (FIG. 7). For example, in JEG-3 cells, PPARγ induced luciferase 1.2-fold in the absence and 2.4-fold in the presence of ciglitazone, whereas the inductions with PPFP were 1.9- and 3.4-fold.

The ANGPTL4 promoter was not induced by either PPARg or PPFP in FRTL-5 cells, but in dog thyrocytes PPFP expression resulted in a 3.5-fold induction in the absence and a 5.2-fold induction in the presence of ciglitazone. The response in N2a cells was qualitatively similar to that in dog thyrocytes, with PPARγ not inducing this promoter but PPFP resulting in inductions of 2.2- and 3.1-fold in the absence and presence of ciglitazone.

Figure 8:
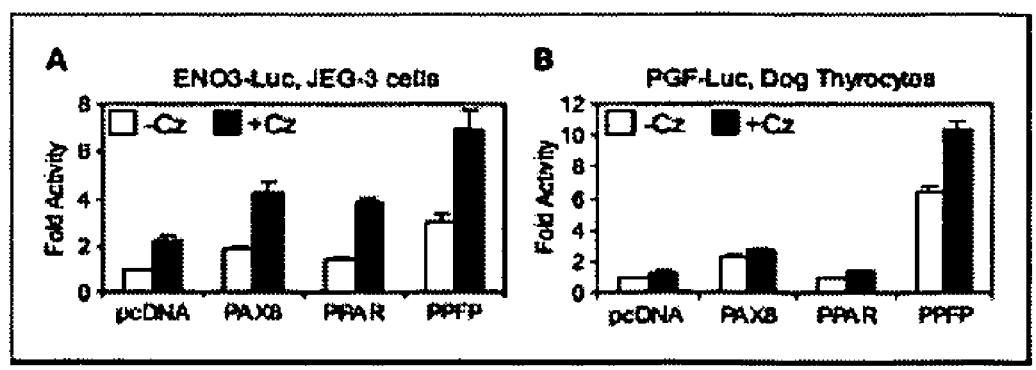
FIG. 8 shows regulation of the ENO3 (FIG. 8A) and PGF (FIG. 8B) promoters.

In JEG-3 cells, the ENO3 promoter was also induced more strongly by PPFP (2.9-fold minus ciglitazone and 6.9-fold plus ciglitazone) than by PPARγ (1.3- and 3.8-fold; FIG. 8A). However, this promoter was not induced by PPARγ, PPFP, or PAX8 in N2a cells, FRTL-5 cells, or dog thyrocytes. The PGF promoter was not induced by PPARγ, PPFP, or PAX8 in any of the cell lines. However, in dog thyrocytes, PPFP caused inductions of 6.4-fold minus ciglitazone and 10-fold plus ciglitazone, compared with no induction by PPARγ and a 2.5-fold induction by PAX8 (FIG. 8B).

TABLE 5

| Annotation source | Term/pathway | Total number of genes with term | Number out of 761 selected genes | P |
|---|---|---|---|---|
| GO | Fatty acid metabolism | 55 | 13 | 1.6E−05 |
|  | Fatty acid β-oxidation | 11 | 6 | 1.6E−05 |
|  | Transport | 421 | 46 | 5.0E−05 |
|  | Amino acid transport | 35 | 9 | 1.6E−04 |
|  | Oxidoreductase activity | 355 | 37 | 6.7E−04 |
| Gen MAPP | Mitochondrial fatty acid β oxidation | 17 | 8 | 2.0E−06 |
|  | Glycogen metabolism | 36 | 10 | 3.3E−05 |
|  | Fatty acid degradation | 22 | 7 | 2.0E−04 |
|  | Glycolysis and gluconeogenesis | 43 | 8 | 3.5E−03 |
| KEGG | Fatty acid biosynthesis (path 2) | 12 | 6 | 3.0E−05 |
|  | Fatty acid metabolism | 61 | 12 | 2.2E−04 |
|  | Valine, leucine, and isoleucine degradation | 39 | 9 | 3.9E−04 |
|  | Benzoate degradation via hydroxylation | 6 | 3 | 3.7E−03 |
|  | Glycolysis/Gluconeogenesis | 56 | 9 | 5.6E−03 |
|  | Propanoate metabolism | 29 | 6 | 6.5E−03 |
|  | β-Alanine metabolism | 21 | 5 | 6.8E−03 |
|  | Pentose phosphate pathway | 22 | 5 | 8.4E−03 |

Pathway Analysis of the PAX8-PPARG Signature Genes

The larger set of 977 probe sets found to be altered with the PAX8-PPARG translocation was analyzed for enriched Gene Ontology terms, Kyoto Encyclopedia of Genes and Genomes pathways, and GenMAPP maps (Table 5). The most substantial enrichment was observed for pathways related to fatty acid metabolism. Induced genes in these pathways include several acyl-CoA dehydrogenases (ACADL, ACADM, ACADS), acetyl-CoA acyltransferases (ACAA1, ACAA2), and hydroxyacyl-CoA dehydrogenases (HADHA, HADHSC), all of which participate in fatty acid h-oxidation. Other metabolic pathways also were enriched, such as Kyoto Encyclopedia of Genes and Genomes pathways valine, leucine, and isoleucine degradation, and glycolysis/gluconeogenesis. PPARg regulates adipogenesis and glucose metabolism.

Bioinformatic Analysis Using Oncomine

The Oncomine data mining platform (Rhodes et al., Neoplasia 2004; 6:1) was used to compare the PPFP(+) and PPFP (−) follicular carcinoma gene expression profiles (Thy203 included), as a means of exploring for differences of potential biological significance between these groups of follicular carcinomas. Genes located on chromosome 3p were found to be overrepresented, with 95 of 341 measured genes on 3p being in the top 20% of the PPFP(+) up-regulated profile (P=5.1E−5, Q=0.002; all other chromosome arms had Q values of at least 0.2). It is contemplated that this is a consequence of the t(2;3)(q13;p25) chromosomal translocation and reflects strong PAX8 regulatory sequences from chromosome 2 exerting effects on chromosome 3p genes or other chromosome structural effects. The genes on 3p that are induced include two genes that are directly involved in fatty acid metabolism—carnitine/acylcarnitine translocase (SLC25A20), which transfers fatty acylcarnitines into mitochondria, and acetyl-CoA acyltransferase 1 (ACAA1), which participates in peroxisomal fatty acid h oxidation.

Recently, it has become clear that miRNAs down-regulate the expression of a large number of genes posttranscriptionally by binding to short sequences in mRNA 3V untranslated regions. Each miRNA may regulate multiple mRNAs, and one mRNA may be regulated by multiple miRNAs. Oncomine uses PicTar (Krek et al., Nat Genet 2005; 37:495) to analyze for miRNA target genes. Putative target genes for four miRNAs are strongly overrepresented among the upregulated genes in PPFP(+) follicular carcinomas: miR-101 (104 of 329 measured target genes are in the top 20% of the PPFP(+) profile, P=2.1E-7, Q=3.6E-5), miR-30A-3P (55 of 160 measured target genes, P=1.1E-5, Q=9.3E-4), miR-200A (81 of 262 measured target genes, P=1.2E-5, Q=6.7E-4), and miR-199A (92 of 309 measured target genes, P=1.7E-5, Q=7.1E-4). Twenty-one up-regulated genes are putative targets for at least three of these four miRNAs, suggesting coordinate regulation. Included in this list are the oncogenes RUNX1/AML1 and SS18; PUM2, which encodes a protein thought to be involved in stem cell proliferation and self renewal; and NRP2, which encodes the vascular endothelial growth factor/PGF receptor neuropilin 2.

Figure 9:
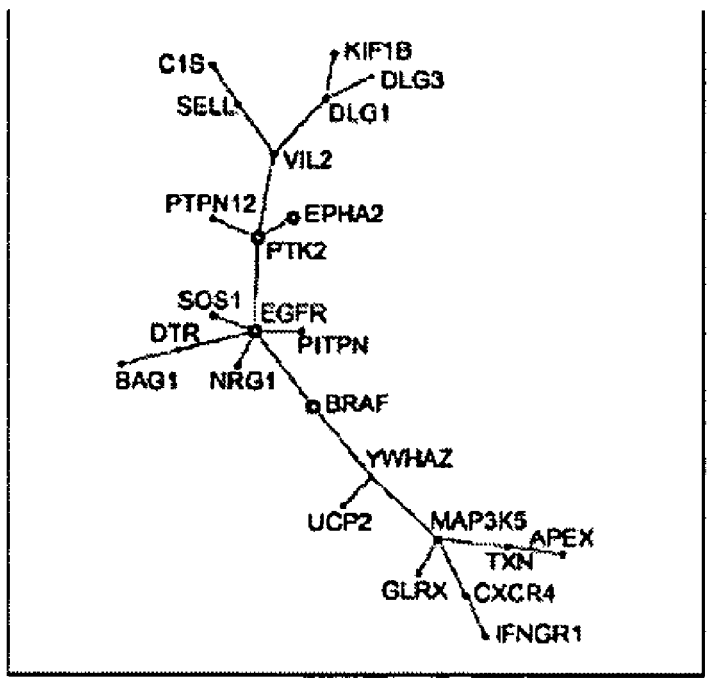
FIG. 9 shows a map of genes regulated by EGFR.

The Oncomine "Interactome" identifies known physically interacting proteins (based up the Human Protein Reference Database; Peri et al., Genome Res 2003; 13:2363) among the differentially expressed genes. This analysis revealed correlations between the expression of PPARγ (which also measures PPFP) and two proteins that can function as PPARγ coactivators, GADD45G (r2=0.85) and NCOA4/ARA70 (r2=0.48). It is contemplated that, in PPFP(+) follicular carcinoma, the PPARγ-like transcriptional activity of PPFP is magnified by increased expression of these proteins. Interactome analysis also revealed that the set of genes with increased transcript expression in PPFP(+) follicular carcinomas includes the epidermal growth factor receptor (EGFR) and ERBB3 oncogene, which dimerizes with EGFR and is amplified in numerous cancers; PTK2, a tyrosine kinase that binds to and helps transmit motility signals from the EGFR; and HBEGF, which binds and activates EGFR with greater potency than EGF. The Interactome analysis also allows one to visualize overall networks of interactions by drawing an interaction map. This reveals that the EGFR is a central node that connects to numerous other up-regulated genes, including the oncogenes BRAF, PTK2, and EPHA2 (FIG. 9).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for diagnosing papillary thyroid cancer in a subject, comprising: a) providing a thyroid tissue sample from a subject suspected of having papillary thyroid cancer; b) detecting an increased the level of expression of claudin 1 mRNA or polypeptide in said sample; c) comparing said level of expression of said claudin 1 mRNA or polypeptide in said sample with a level of expression of claudin 1 mRNA or polypeptide in a non-cancerous thyroid sample; and d) diagnosing papillary carcinoma thyroid cancer in said subject when an increased level of expression of said claudin 1 relative to the level of expression in non-cancerous thyroid samples is present in said sample.

2. The method of claim 1, wherein said detecting comprises immunohistochemistry.

3. The method of claim 1, wherein said subject comprises a human subject.

4. The method of claim 1, wherein said sample comprises tumor tissue.

* * * * *

UNITED STATES PATENT AND TRADEMARK OFFICE
CERTIFICATE OF CORRECTION

PATENT NO. : 7,598,052 B2
APPLICATION NO. : 11/545586
DATED : October 6, 2009
INVENTOR(S) : Thomas Giordano et al.

Page 1 of 1

It is certified that error appears in the above-identified patent and that said Letters Patent is hereby corrected as shown below:

IN THE CLAIMS:

Column 69, Claim 1, Line 5, after detecting and before the please delete "an increased".

Signed and Sealed this

Eighth Day of December, 2009

David J. Kappos
*Director of the United States Patent and Trademark Office*

```
                              SEQUENCE LISTING

<160> NUMBER OF SEQ ID NOS: 19

<210> SEQ ID NO 1
<211> LENGTH: 16
<212> TYPE: DNA
<213> ORGANISM: Artificial Sequence
<220> FEATURE:
<223> OTHER INFORMATION: Synthetic

<400> SEQUENCE: 1
cgacagactg cacagg                                                         16

<210> SEQ ID NO 2
<211> LENGTH: 16
<212> TYPE: DNA
<213> ORGANISM: Artificial Sequence
<220> FEATURE:
<223> OTHER INFORMATION: Synthetic

<400> SEQUENCE: 2
tgacttctgg tgccat                                                         16

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ggccaaggct tcatgacaa                                                      19

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
aactcaaact tgggctccat aaag                                                24

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
taaagagcct gcgaaagcct tttggtg                                             27

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
```
aaagcacctt cgcacggatg                                                    20

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
acggagctga tcccaaagtt gg                                                 22

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
tccttgtccc ccgtgatct                                                     19

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tggccggaaa gaacaatgtc                                                    20

<210> SEQ ID NO 10
<211> LENGTH: 29
<212> TYPE: DNA
<213> ORGANISM: Artificial Sequence
<220> FEATURE:
<223> OTHER INFORMATION: Synthetic

<400> SEQUENCE: 10
ccctcacact ttgccatttg cttgtactg                                          29

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
ggaccgagaa taagtccaag tttg                                               24

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
agctgctccc gccttacac                                                     19

<210> SEQ ID NO 13
<211> LENGTH: 23
<212> TYPE: DNA
<213> ORGANISM: Artificial Sequence

```
<220> FEATURE:
<223> OTHER INFORMATION: Synthetic

<400> SEQUENCE: 13
atgccatcct gggcgtgtcc ttg                                    23

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
accctgcccc acccttac                                          18

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
ggaatggatg ggatcacaaa taat                                   24

<210> SEQ ID NO 16
<211> LENGTH: 29
<212> TYPE: DNA
<213> ORGANISM: Artificial Sequence
<220> FEATURE:
<223> OTHER INFORMATION: Synthetic

<400> SEQUENCE: 16
tccatggccc tagagcactt ctaagcaga                              29

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
catggtgctg gtgctgttgt                                        20

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
aggttgcttt tattccaaga actctgt                                27

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
caagcaggcg ccaatggtat ctgg                                   24
```